US012760355B2

(12) United States Patent
Pardee et al.

(10) Patent No.: US 12,760,355 B2
(45) Date of Patent: Oct. 13, 2026

(54) ELECTROCHEMICAL INTERFACE FOR MOLECULAR CIRCUIT-BASED OUTPUTS

(71) Applicant: The Governing Council of the University of Toronto, Toronto (CA)

(72) Inventors: Keith Pardee, Toronto (CA); Shana O. Kelley, Toronto (CA); Sarah J. Smith, Lewisburg, PA (US); Peivand S. Mousavi, Waterloo (CA); Jenise B. Chen, Toronto (CA); Wenhan Liu, London (CA)

(73) Assignee: The Governing Council of the University of Toronto, Toronto (CA)

(*) Notice: Subject to any disclaimer, the term of this patent is extended or adjusted under 35 U.S.C. 154(b) by 1051 days.

(21) Appl. No.: 17/773,542

(22) PCT Filed: Oct. 29, 2020

(86) PCT No.: PCT/CA2020/051464
§ 371 (c)(1),
(2) Date: Apr. 29, 2022

(87) PCT Pub. No.: WO2021/081656
PCT Pub. Date: May 6, 2021

(65) Prior Publication Data

US 2023/0175044 A1 Jun. 8, 2023

Related U.S. Application Data

(60) Provisional application No. 62/929,452, filed on Nov. 1, 2019.

(51) Int. Cl.
*C12Q 1/6825* (2018.01)
*G01N 27/327* (2006.01)
(Continued)

(52) U.S. Cl.
CPC ....... *C12Q 1/6825* (2013.01); *G01N 27/3276* (2013.01); *G01N 27/3277* (2013.01); *G01N 27/416* (2013.01); *C12Q 1/6876* (2013.01)

(58) Field of Classification Search
None
See application file for complete search history.

(56) References Cited

U.S. PATENT DOCUMENTS 6,391,558 B1 * 5/2002 Henkens .............. C12Q 1/6825 422/50
2009/0270266 A1 * 10/2009 Kelley .............. G01N 33/5438 977/762

(Continued)

FOREIGN PATENT DOCUMENTS

WO 2010019414 2/2010
WO 2015/085209 6/2015

OTHER PUBLICATIONS

Alligrant et al. (2013) "Electrochemical detection of individual DNA hybridization events," Lab on a Chip, (13)3: 349-354.

(Continued)

*Primary Examiner* — Brian R Gordon
(74) *Attorney, Agent, or Firm* — Edward J. Baba; Bozicevic, Field & Francis LLP

(57) ABSTRACT

Described herein is an RNA detection system and methods of using for detecting one or more RNA target molecules. The system comprises an upstream molecular circuitry system comprising one or more RNA toehold switch-based sensors that are activated in the presence of an RNA target molecule to produce a restriction enzyme which cleaves and releases a redox active reporter molecule that binds a capture molecule bound to an electrode, thereby producing a detectable electrochemical signal.

7 Claims, 6 Drawing Sheets

Specification includes a Sequence Listing.

(51) Int. Cl.
*G01N 27/416* (2006.01)
*C12Q 1/6876* (2018.01)

(56) References Cited

U.S. PATENT DOCUMENTS

| | | | | |
|---|---|---|---|---|
| 2012/0058547 A1* | 3/2012 | Hsing | C12Q 1/6823 | 435/287.2 |
| 2012/0288857 A1* | 11/2012 | Livak | C12Q 1/6818 | 435/6.12 |
| 2013/0288923 A1* | 10/2013 | Vallee-Belisle | C12Q 1/6825 | 506/9 |
| 2018/0217148 A1* | 8/2018 | Ingber | G01N 33/535 | |
| 2020/0025757 A1* | 1/2020 | Gopinath | G01N 33/54373 | |
| 2022/0317082 A1* | 10/2022 | Soleymani | G01N 27/3276 | |

OTHER PUBLICATIONS

Cameron et al. (2014) "A brief history of synthetic biology," Nat Rev Microbiol, 12: 381-390.
Cheng et al. (2012) "Synthetic Biology: An Emerging Engineering Discipline," Annu Rev Biomed Eng, 14: 155-178.
Das et al. (2012) "An ultrasensitive universal detector based on neutralizer displacement," Nat Chem, 4: 642-648.
Das et al. (2011) "Protein Detection Using Arrayed Microsensor Chips: Tuning Sensor Footprint to Achieve Ultrasensitive Readout of CA-125 in Serum and Whole Blood," Anal Chem, 83(4):1167-1172.
Davis et al. (2011) "Design, construction and characterization of a set of insulated bacterial promoters," Nucleic Acids Res, 39(3):1131-1141.
Fan et al. (2003) "Electrochemical interrogation of conformational changes as a reagentless method for the sequence-specific detection of DNA," Proc Natl Acad Sci, 100(16): 9134-9137.
Fossati et al. (2014) "Reconstitution of a 10-gene pathway for synthesis of the plant alkaloid dihydrosanguinarine in *Saccharomyces cerevisiae*, " Nat Commun, 5(3283): 1-11.
Garcia et al. (2018) "Co-occurrence of mcr-1, mcr-4 and mcr-5 genes in multidrug-resistant STIO Enterotoxigenic and Shiga toxin-producing *Escherichia coli* in Spain (2006-2017)," Int J Antimicrob Agents, 52(1): 104-108.
Gootenberg et al. (2017) "Nucleic acid detection with CRISPR-Cas13a/C2c2," Author Manuscript, Science, 356 (6336): 438-442.
Green et al. (2014) "Toehold switches: de-novo-designed regulators of gene expression," Cell, 159: 925-939.
Green et al. (2017) "Complex cellular logic computation using ribocomputing devices," Nature, 548: 117-121.
Huang et al. (2018) "BioBits™ Explorer: A modular synthetic biology education kit," Sci Adv, 4(8): 1-10.
Jewett et al. (2008) "An integrated cell-free metabolic platform for protein production and synthetic biology," Mol Syst Biol, 4(220): 1-8.
Karig et al. (2012) "Expression optimization and synthetic gene networks in cell-free systems," Nucleic Acids Res, 40 (8): 3763-3774.
Keasling, J. D. (2012) "Synthetic biology and the development of tools for metabolic engineering," Metab Eng, 14(3): 189-195.
Khan et al. (2010) "In Situ, Label-Free DNA Detection Using Organic Transistor Sensors," Adv Mater, 22(40): 4452-4456.
Kitada et al. (2018) "Programming gene and engineered-cell therapies with synthetic biology," Manuscript, Science, 359(6376): 1-49.
Kotula et al. (2014) "Programmable bacteria detect and record an environmental signal in the mammalian gut," Proc Natl Acad Sci, 111(13): 4838-4843.
Kuang et al. (2010) "Biomimetic Chemosensor: Designing Peptide Recognition Elements for Surface Functionalization of Carbon Nanotube Field Effect Transistors," ACS Nano, 4(1): 452-458.
Li et al. (2000) "Using molecular beacons as a sensitive fluorescence assay for enzymatic cleavage of single-stranded DNA," Nucleic Acids Res, 28(11): 1-6.
Liu et al. (2012) "Aptamer-based Origami Paper Analytical Device for Electrochemical Detection of Adenosine," Author Manuscript, Angew Chemie Int Ed, 51(28): 1-9.
Mao et al. (2018) "Probiotic strains detect and suppress cholera in mice," Sci Transl Med, 10(445): 1-8.
Pardee et al. (2014) "Paper-Based Synthetic Gene Networks," Cell, 159(4): 940-954.
Pardee et al. (2016) "Portable, On-Demand Biomolecular Manufacturing," Cell, 167(1): 248-259.
Pardee et al. (2016) "Rapid, Low-Cost Detection of Zika Virus Using Programmable Biomolecular Components," Cell, 165(5): 1255-1266.
Patolsky et al. (2001) "Detection of single-base DNA mutations by enzyme-amplified electronic transduction," Nat Biotechnol, 19: 253-257.
Sage et al. (2014) "Ultrasensitive Electrochemical Biomolecular Detection Using Nanostructured Microelectrodes," Acc Chem Res, 47(8): 2417-2425.
Shimizu et al. (2001) "Cell-free translation reconstituted with purified components," Nat Biotechnol, 19:751-755.
Shin et al. (2012) "Genome Replication, Synthesis, and Assembly of the Bacteriophage T7 in a Single Cell-Free Reaction," ACS Synth Biol, 1(9): 408-413.
Slinker et al. (2010) "Multiplexed DNA-Modified Electrodes," Author Manuscript, J Am Chem Soc, 132(8): 2769-2774.
Smanski et al. (2016) "Synthetic biology to access and expand nature's chemical diversity," Author Manuscript, Nat Rev Microbiol, 14(3): 135-149.
Smith et al. (2017) "Incorporation of synthetic, toe-hold based gene circuits for the development of electrochemical sensors for rapid disease diagnostics," Abstracts of Papers, 254th ACS National Meeting & Exposition, Washington, DC, USA, Aug. 20-24, 2017, 254: 332.
Soleymani et al. (2009) "Programming the detection limits of biosensors through controlled nanostructuring," Nat Nanotechnol, 4: 844-848.
Stark et al. (2018) "BioBits ™ Bright: A fluorescent synthetic biology education kit," Sci Adv, 4(8): 1-10.
Takahashi et al. (2018) "A low-cost paper-based synthetic biology platform for analyzing gut microbiota and host biomarkers," Nat Commun, 9(3347): 1-12.
Tang et al. (2008) "Ultrasensitive Electrochemical Immunosensor for Clinical Immunoassay Using Thionine-Doped Magnetic Gold Nanospheres as Labels and Horseradish Peroxidase as Enhancer," Anal Chem, 80(5): 1582-1588.
Wen et al. (2017) "A Cell-Free Biosensor for Detecting Quorum Sensing Molecules in P. aeruginosa-Infected Respiratory Samples," ACS Synth Biol, 6: 2293-2301.
Yehl et al. (2017) "Scaling Computation and Memory in Living Cells," Author Manuscript, Curr Opin Biomed Eng, 4: 143-151.
Zadeh et al. (2011) "NUPACK: Analysis and design of nucleic acid systems," Journal of Computational Chemistry, 32 (1): 170-173.
Zhang et al. (2018) "Molecular detection of colistin resistance genes (mcr-1, mcr-2 and mcr-3) in nasal/oropharyngeal and anal/cloacal swabs from pigs and poultry," Sci Rep, 8(3705): 1-9.
Zuo et al. (2009) "High Specificity, Electrochemical Sandwich Assays Based on Single Aptamer Sequences and Suitable for the Direct Detection of Small-Molecule Targets in Blood and Other Complex Matrices," Author Manuscript, J Am Chem Soc, 131(20): 6944-6945.
International Search Report dated Jan. 4, 2021 for PCT application Serial No. PCT/CA2020/051464. 3 pgs.
Written Opinion dated Jan. 4, 2021 for PCT application Serial No. PCT/CA2020/051464. 4 pgs.
International Preliminary Report on Patentability dated May 3, 2022 for PCT application Serial No. PCT/CA2020/051464. 4 pgs.
Chen et al., "Ultrasensitive amperometric aptasensor for the epithelial call adhesion molecule by using target-driven toehold-mediated DNA recycling amplification", Microchimica Acta, Springer Vienna, vol. 185, No. 3, Mar. 1, 2018; pp. 1-8.

(56) References Cited

OTHER PUBLICATIONS

Rowe et al., "Fabrication of Electrochemical-DNA Biosensors for the Reagentless Detection of Nucleic Acids, Proteins and Small Molecules", Journal of Visualized Experiments, No. 52, Jun. 1, 2011.

Sadat Mousavi et al., "A multiplexed, electrochemical interface for gene-circuit-based sensors", Nature Chemistry, Nature Publishing Group UK, London, vol. 12, No. 1, Nov. 25, 2019; pp. 48-55.

Wang et al., "Nucleic acid-based ratiometric electrochemiluminescent, electrochemical and photoelectrochemical biosensors: a review", Microchimica Acta, Springer Vienna, vol. 186, No. 7, Jun. 10, 2019, pp. 1-19.

European Application 20882629.7, Extended European Search Report dated Nov. 30, 2023.

Duan, et al. (2012) "Quantification of the affinities and kinetics of protein interactions using silicon nanowire biosensors." Nat Nanotechnol. 7 (6): 401-407. doi:10.1038/nnano.2012.82.

Lam, et al. (2012) "Polymerase Chain Reaction-Free, Sample-to-Answer Bacterial Detection in 30 Minutes with Integrated Cell Lysis." Anal Chem. 84: 21-25.

Lerner, et al. (2012) "Hybrids of a Genetically Engineered Antibody and a Carbon Nanotube Transistor for Detection of Prostate Cancer Biomarkers." ACS Nano. 6 (6): 5143-5149. doi:10.1021/nn300819s.

Malhotra, et al. (2011) "Ultrasensitive Electrochemical Immunosensor for Oral Cancer Biomarker IL-6 using Carbon Nanotube Forest Electrodes and Multilabel Amplification Ruchika." Anal Chem. 82 (8): 3118-3123. doi:10.1021/ac902802b.

Mani, et al. (2009) "Ultrasensitive Immunosensor for Cancer Biomarker Proteins Using Gold Nanoparticle Film Electrodes and Multienzyme-Particle Amplification." ACS Nano. 3(3): 585-594.

Mannoor, et al. (2010) "Electrical detection of pathogenic bacteria via immobilized antimicrobial peptides." PNAS. 107 (45): 19207-19212. doi:10.1073/pnas.1008768107.

Santiago, et al. (2018) "Performance of the Trioplex real-time RT-PCR assay for detection of Zika, dengue, and chikungunya viruses." Nat Commun. 9 (1391): 1-10. doi:10.1038/s41467-018-03772-1.

Swensen, et al. (2009) "Real-Time Monitoring of Cocaine in Undiluted Blood Serum via a Microfluidic, Electrochemical Aptamer-Based Sensor." JACS. 131 (12): 4262-4266.

Vasilyeva, et al. (2011) "Direct Genetic Analysis of Ten Cancer Cells: Tuning Sensor Structure and Molecular Probe Design for Efficient mRNA Capture**. " Angew. Chem. Int. Ed. 50: 4137-4141. doi:10.1002/anie.201006793.

Zheng, et al. (2005) "Multiplexed electrical detection of cancer markers with nanowire sensor arrays." Nat Biotechnol., 23 (10): 1294-1301. doi:10.1038/nbt1138.

* cited by examiner inhibitorDNA
reporterDNA
Enzyme cut site
AciI
captureDNA
Au surface Current (nA)
Potential (V)

AciI
Neg. Cont.
Current (nA)
Time (min)

T7
DNA
RNA
Ribosome
Fold turn-on
Restriction enzyme system
AciI
BanII
BglII
BsaAI
BstEII
ClaI
EcoRV
HincII
NcoI
PstI reporterDNA + restriction enzyme
captureDNA
Current (nA)

Coding sequences
RNA
Active enzymes
Folc turn-on

ELECTROCHEMICAL INTERFACE FOR MOLECULAR CIRCUIT-BASED OUTPUTS

CROSS-REFERENCE TO RELATED APPLICATIONS

This application is the national phase under 35 U.S.C. § 371 of International Application Serial No. PCT/CA2020/051464, which has an International filing date of Oct. 29, 2020, which claims priority to U.S. Provisional Application Ser. No. 62/929,452, filed on Nov. 1, 2019, which application is incorporated herein by reference in its entirety.

INCORPORATION BY REFERENCE OF SEQUENCE LISTING PROVIDED AS A TEXT FILE

A Sequence Listing is provided herewith in a text file, ROBI-018_017978-0205_Seqlist_ST25, created on Nov. 10, 2022 and having a size of 57,434 bytes of file. The contents of the text file are incorporated herein by reference in its entirety.

FIELD

The present invention relates to a molecular circuitry-based detection system for the identification of a target molecule and method of uses thereof.

BACKGROUND

The field of synthetic biology uses genetically-encoded tools to create biological systems with new functions (1,2). Work to date has generated organisms with engineered metabolic pathways for bioproduction (3,4), embedded synthetic logic and memory (5-7) and the capacity to sense and respond (8,9). Despite being poised to revolutionize many aspects of modern life, this cell-based approach requires that all processes be laboriously encoded within a living organism (10), and introduces significant complexity into the application of synthetic biology including limits to the distribution of these tools over concerns of biosafety. Recent efforts have aimed to tackle this long-standing challenge by creating cell-free synthetic biology applications that use the enzymes of transcription and translation (11-13) to provide a biosafe format for applications ranging from point-of-care diagnostics to biomanufacturing to classroom education (14-20). Cell-free systems are particularly advantageous as they can be freeze-dried for distribution without refrigeration and so the central motivation for many of these projects has been to provide portable diagnostics/sensors for global health, agriculture, national security and other applications that would benefit from sensing outside of laboratory settings. Sensors used in these and conventional synthetic biology studies have relied on the expression of optical reporter proteins (e.g. colorimetric, fluorescence), which, while successful, generally provide the capacity for one, at most two or three, reporter signals from a single reaction.

There is therefore a need for a molecular circuit-to-electrode interface that allows for the output from engineered, cell-free molecular circuits to be transformed into a signal that can be detected electrochemically.

SUMMARY

The present description relates to a detection or reporter system, that comprises a molecular circuit, which can be used alone or in a multiplexed fashion. Upstream molecular circuits comprise biological sensors that can detect specific inputs, which triggers a corresponding reporter system to produce an electrochemical output.

In some embodiments described herein, is a detection system comprising:

a. an upstream molecular circuitry system that is activated in the presence of a target molecule to produce a reporter molecule;
b. a capture molecule bound to an electrode;
wherein the reporter molecule specifically binds to the capture molecule bound to the electrode to produce or reduce a detectable electrochemical signal.

In some embodiments described herein, is a detection system comprising:

a. an upstream molecular circuitry system that is activated in the presence of a target molecule to produce an activator;
b. a reporter system; and
c. a capture molecule bound to an electrode;
wherein the activator activates the reporter system to produce or specifically release a reporter molecule and wherein the reporter molecule specifically binds to the capture molecule bound to the electrode to produce or reduce a detectable electrochemical signal.

In some embodiments described herein, is a detection system comprising:

a. an upstream molecular circuitry system comprising one or more different RNA toehold switch-based sensor(s), wherein each RNA toehold switch is specific to a target molecule that is an RNA sequence within a sample, and comprises an mRNA sequence encoding a distinct activator that is a restriction enzyme;
b. one or more reporter system(s), wherein each reporter system comprises a reporter molecule that is a reporterDNA, bound to an inhibitory single-stranded DNA that is an iDNA, wherein said reporterDNA is coupled to a redox active molecule, and wherein said reporterDNA and iDNA comprise a sequence recognized by said restriction enzyme;
c. one or more capture molecules, wherein each capture molecule that is a captureDNA, is coupled to an electrode and comprises a sequence complementary to said reporterDNA;
wherein the restriction enzyme activates the reporter system by specifically releasing the reporterDNA from the iDNA and wherein the reporterDNA specifically binds to the captureDNA, to produce an electrochemical signal detected by the electrode.

In some embodiments described herein, is a method of detecting a target molecule comprising:

a. providing the molecular-based detection system as defined herein;
b. contacting said system with a sample; and
c. detecting an electrochemical signal, wherein detection of said signal indicates the presence of the target molecule.

In some embodiments described herein, is a method of detecting a target molecule comprising:

a. providing the molecular-based detection system as defined herein;
b. contacting said system with a sample; and
c. detecting an electrochemical signal, wherein detection of said signal indicates the presence of the target molecule.

In some embodiments described herein, is a method for detecting multiple RNA sequences within a sample, said method comprising the steps of:

a. incubating the sample with a set of synthetic RNA-based sensors;
b. binding of an RNA sequence within said sample to a complementary synthetic RNA toehold switch and activating said synthetic RNA toehold switch;
c. translating mRNA regulated by said synthetic RNA toehold switch to a protein;
d. binding of said translated protein to a redox reporter molecule and releasing said molecule;
e. binding of said redox reporter molecule to an electrode-bound capture molecule; and
f. generating an electrochemical signal from said electrode.

BRIEF DESCRIPTION OF THE DRAWINGS

In the appended drawings:

FIG. 3A: Electrochemical detection of restriction enzyme reporters. A schematic of the electrochemical detection chip designed to detect (in triplicate) reporterDNA generated by five restriction enzyme-based reporters in parallel FIG. 3B: Scanning electron microscopy images of nanostructured microelectrodes. Scale bar is 50 μm.

FIG. 3C: In solution, restriction enzymes cleave a reporter/inhibitor DNA duplex. The reporterDNA strand carrying methylene blue (blue circle) is then recruited to the surface of the electrode through duplex formation with conjugated captureDNA, bringing the electrochemical reporter molecule to the electrode surface.

FIG. 3D: Representative square wave voltammetry data showing the measured current with (black) and without (gray) restriction enzyme expression.

FIG. 3E: On-chip square wave voltammetry measurements in real-time as the restriction enzyme AciI is expressed.

FIG. 3F: Fold turn-on of measured peak current in the presence of restriction enzymes for each of the ten respective reporterDNA-captureDNA systems. Data was normalized to the measured current in the absence of DNA encoding each restriction enzyme, represented as dotted line.

FIG. 3G: Electrochemical reporterDNA-captureDNA systems were tested to evaluate cross-reactivity between respective restriction enzyme reporters. Values on heat map are average of triplicates at 30 min.

FIG. 3H: Using methylated DNA, fold turn-on from the co-expression of five restriction enzyme reporters in a single solution and measured on a single chip. Data was normalized to the measured current in the absence of DNA encoding each restriction enzyme, represented as dotted line. Data represents the mean±SE of three replicates. All electrochemical measurements were performed with square wave voltammetry and peak current is used for calculation of fold turn-on.

FIG. 4B: Toehold switches specific to synthetic RNA sequences were designed to control the expression of six different restriction enzyme-based reporters. RNA-dependent activation of toehold switches induces electrochemical signaling. Dotted line indicates switch alone negative controls. All electrochemical measurements were performed with square wave voltammetry and peak current is used for calculation of fold turn-on.

SEQUENCE LISTING

Figure 1:
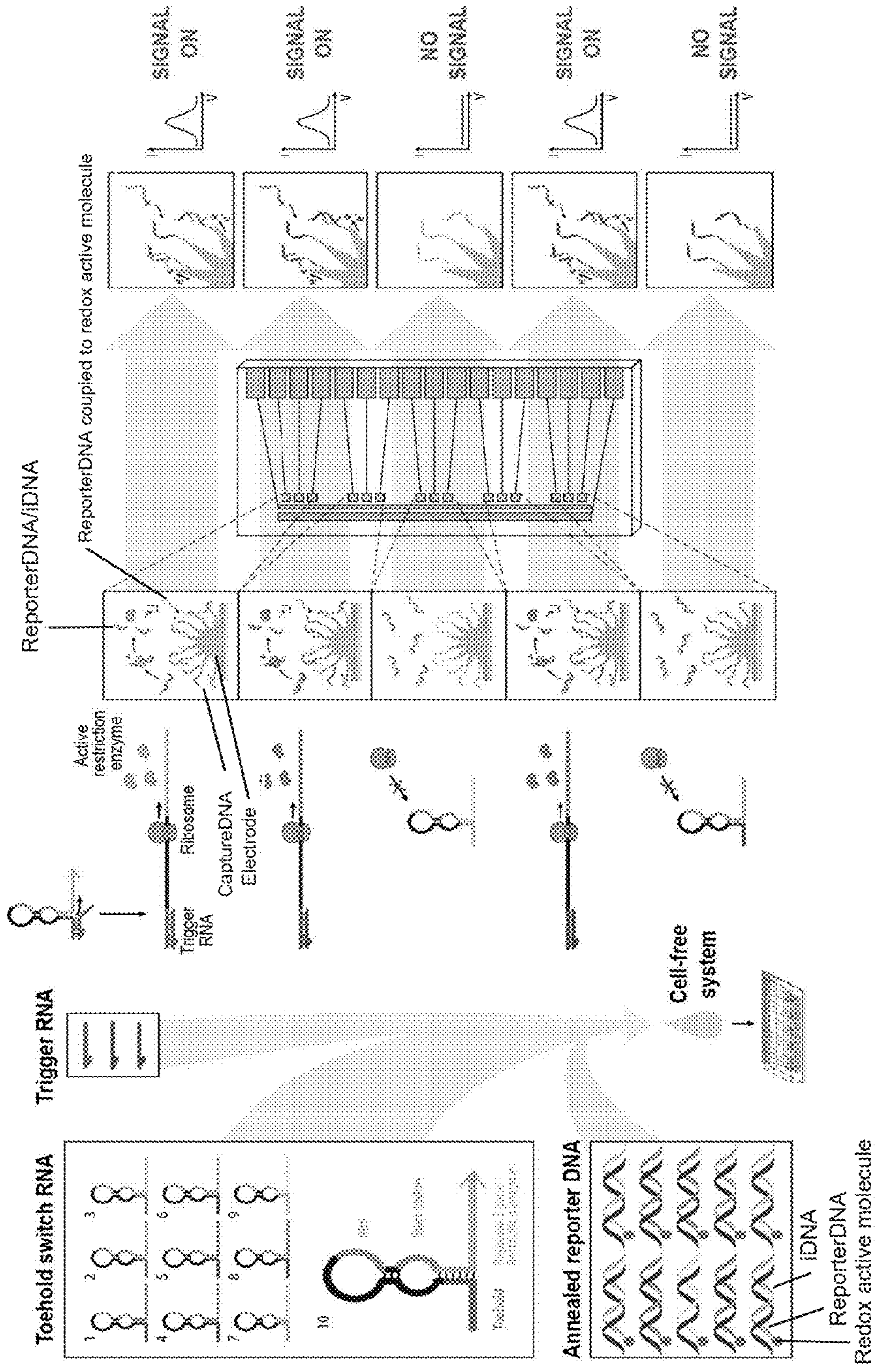
FIG. 1: A molecular circuit-electrode interface for cell-free synthetic gene networks. By combining cell-free transcription and translation systems with engineered molecular circuits on nanostructured microelectrodes, distinct and multiplexed output signals can be tracked in parallel. Here we describe this approach using toehold switch-based RNA sensors, which, in the presence of trigger RNA, express one of ten restriction enzyme-based reporters. Upon sensor activation, expressed restriction enzymes cleave annealed reporterDNA, which is free floating in cell-free reactions, releasing the redox reporter-labelled reporterDNA (blue circle). Nanostructured microelectrodes with conjugated captureDNA then recruit the redox-active reporterDNA to their surface, generating an electrochemical signal. Each toehold switch is engineered to produce a unique restriction enzyme-based reporter that is coupled to a distinct reporterDNA and captureDNA pair for multiplexed signaling.

This application contains a Sequence Listing in computer readable form created Oct. 10, 2019 having a size of about 51 kb. The computer readable form is incorporated herein by reference.

TABLE 1

Sequence Listing of Successfully Expressed Restriction Enzymes in a Cell-Free System codon optimized for *E. coli* expression and modified to remove self-cutting sequences)

| SEQ ID NO: | GenBank ID | Description |
|---|---|---|
| 1 | HQ327694 | AciI |
| 2 | AF247972 | AgeI |
| 3 | ADJ68010 | AluI |
| 4 | HQ327698 | ApaI |
| 5 | NZ_LCYI01000022 | BamHI |
| 6 | HM569709 | BanII |
| 7 | CP007640.1 | BglII |
| 8 | AF522187 | BpmI |
| 9 | HQ446231 | BsaAI |
| 10 | EU386360 | BsaHI |
| 11 | HQ636106 | BstEII |
| 12 | JF323047 | ClaI |
| 13 | DQ491002 | CviQI |
| 14 | Y00449 | DdeI |
| 15 | WP_081407150 | EcoRI |
| 16 | P04390 | EcoRV |
| 17 | NEBM150 | HhaI |
| 18 | X54197 | HincII |
| 19 | M22862 | HinfI |
| 20 | JF432060 | MscI |
| 21 | AF068761 | NcoI |
| 22 | AY462277 | NheI |
| 23 | DQ242471 | NotI |
| 24 | AAA25673 | PstI |
| 25 | Q53608 | SalI |
| 26 | JF432057 | SfoI |
| 27 | U44748 | XmnI |

TABLE 2

DNA sequences used for the electrochemical detection system

| Enzyme | DNA Strand Type | 5' Modification | Sequence | 3' Modification |
|---|---|---|---|---|
| AciI | Capture | Thiol | CTAGCAGTACACCG (SEQ ID NO: 40) | |
| | Inhibitor | | CTAGCAGAACACCGCGGTTCACGTCCG (SEQ ID NO: 41) | |
| | Reporter | | CGGACGTGAACCGCGGTGTACTGCTAG (SEQ ID NO: 42) | Amine |
| BanII | Capture | | GGCTCCTCGAGTATGC (SEQ ID NO: 43) | Thiol |
| | Inhibitor | | ACTGAGAACGTGGGGCTCCTCGAGTATGC (SEQ ID NO: 44) | |
| | Reporter | Amine | GCATACTCGAGGAGCCCCACGTTCTCAGT (SEQ ID NO: 45) | |
| BglII | Capture | Thiol | GCTTGAGAACTAGATC (SEQ ID NO: 46) | |
| | Inhibitor | | GCTTGAGAACTAGATCTAAGCACGTCCAGT (SEQ ID NO: 47) | |
| | Reporter | | ACTGGACGTGCTTAGATCTAGTTCTCAAGC (SEQ ID NO: 48) | Amine |

TABLE 2-continued

DNA sequences used for the electrochemical detection system

| Enzyme | DNA Strand Type | 5' Modification | Sequence | 3' Modification |
|---|---|---|---|---|
| BsaAI | Capture | Thiol | CGTAGGGATCATAC (SEQ ID NO: 49) | |
| | Inhibitor | | CGTAGGGATAATACGTGAGCTCACGTGCA (SEQ ID NO: 50) | |
| | Reporter | | TGCACGTGAGCTCACGTATGATCCCTACG (SEQ ID NO: 51) | Amine |
| BstEII | Capture | Thiol | CACATCGTCATGGTGAC (SEQ ID NO : 52) | |
| | Inhibitor | | CACATCGACATGGTGACCCGATGACCTCGC (SEQ ID NO: 53) | |
| | Reporter | | GCGAGGTCATCGGGTCACCATGACGATGTG (SEQ ID NO: 54) | Amine |
| ClaI | Capture | Thiol | GCAACTGAACAATCG (SEQ ID NO: 55) | |
| | Inhibitor | | GCAACTGTACAATCGATGACTCAGCACCG (SEQ ID NO: 56) | |
| | Reporter | | CGGTGCTGAGTCATCGATTGTTCAGTTGC (SEQ ID NO: 57) | Amine |
| EcoRV | Capture | Thiol | TGCCTGGATTTGAT (SEQ ID NO: 58) | |
| | Inhibitor | | TGCCTGGATTAGATATCCGTCGAGGAGAC (SEQ ID NO: 59) | |
| | Reporter | | GTCTCCTCGACGGATATCAAATCCAGGCA (SEQ ID NO: 60) | Amine |
| HincII | Capture | Thiol | GTCGAGGTACTGTT (SEQ ID NO: 61) | |
| | Inhibitor | | GTCGAGGTAATGTTGACGATCCTGAGCGA (SEQ ID NO: 62) | |
| | Reporter | | TCGCTCAGGATCGTCAACAGTACCTCGAC (SEQ ID NO: 63) | Amine |
| NcoI | Capture | Thiol | CGAACACGTGACCATG (SEQ ID NO: 64) | |
| | Inhibitor | | CGAACACGTGACCATGGTGCAGCATATGG (SEQ ID NO: 65) | |
| | Reporter | | CCATATGCTGCACCATGGTCACGTGTTCG (SEQ ID NO: 66) | Amine |
| PstI | Capture | Thiol | AGGCATGTCACCTGCA (SEQ ID NO: 67) | |
| | Inhibitor | | AGGCATGTCACCTGCAGGAGCTTCAGAAC (SEQ ID NO: 68) | |
| | Reporter | | GTTCTGAAGCTCCTGCAGGTGACATGCCT (SEQ ID NO: 69) | Amine |

TABLE 3

Synthetic Toehold Switch and Trigger Sequences for Unique Restriction Enzymes

| SEQ ID NO: | Toehold Switch Name | SEQ ID NO: | Paired Reporter Enzyme |
|---|---|---|---|
| 28 | Switch 1 | 29 | AciI |
| 30 | Switch 2 | 31 | BanII |
| 32 | Switch 3 | 33 | BstEII |
| 34 | Switch 4 | 35 | ClaI/AciI |
| 36 | Switch 5 | 37 | EcoRV |
| 38 | Switch 6 | 39 | HincII |

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "upstream molecular circuitry system" (also referred to as a gene circuit) refers to an engineered composition that comprises at least one nucleic acid material or construct and can perform a function including, but not limited to sensing, and a regulatory function. An input activates the upstream molecular circuitry system to produce an output. The nucleic acid material or construct (DNA, RNA) can be naturally occurring or synthetic. The upstream system can be a gene expression system wherein the system regulates transcription, translation or cleavage (e.g. synthetic RNA or DNA toehold switch-based sensor, an aptamer-based RNA or DNA switch-based sensor, an inducible transcription system, a riboregulated toehold-gated guide RNA (gRNA) switch-based sensor, or a system for generating a gRNA).

As used herein, the term "target molecule" refers to a small molecule or at least one nucleic acid material such as DNA or RNA.

As used herein, the term "activator" refers to an output produced by the upstream molecular circuitry system and includes, for example, a protein such as a nuclease, a CRISPR associated (Cas) protein, DNAs and RNAs that can cleave nucleic acids or any other molecule with specific nuclease activity. The protein can also be a restriction enzyme which is EcoRV, AciI, ClaI, BanII, BsaAI, BglII, BstEII, HincII, NcoI, or PstI or a Cas protein. The activator can also be a DNAzyme (e.g. deoxyribozyme or catalytic DNA) or RNAzyme (e.g. ribozyme or catalytic RNA). When used in the multiplex context, each activator (for example, restriction enzymes) are selected to provide orthogonal signalling. In certain embodiments, the activator comprises an enzyme (e.g. any oxidase, reductase, or oxidoreductase).

As used herein, the term "reporter system" refers to an engineered composition that is activated by the activator to produce or release a reporter molecule. For example, the reporter system can be a substrate for a nuclease generated by upstream molecular circuitry system.

As used herein, the term "reporter molecule" refers to a molecule (e.g. may be within the reporter system) that can be activated or produced by the activator or the upstream molecular circuitry system. For example, the reporter molecule could be a single-stranded DNA (reporterDNA) or a protein, such as an antibody or an antigen. In certain embodiments, the reporter molecule could be inactive in its bound state and could be released to its active state by an activator. For example, the reporterDNA could be hybridized to a complementary single-stranded DNA (iDNA) in its inactive state. In other embodiments, the reporter molecule can be coupled to a redox active molecule and can bind a capture molecule in its active state. The reporter molecule coupled to a redox active molecule can be referred to as a redox active reporter or redox active reporter molecule. In certain embodiments, the redox active reporter comprises an enzyme cofactor and is enzymatically produced. In other embodiments, the reporter molecule comprises an enzyme (e.g. any oxidase, reductase, or oxidoreductase).

As used herein, the terms "redox active molecule" or "electrochemically active molecule" refer to a molecule or chemical that experiences reduced or oxidized states, which is characterized by the transfer of electrons. For example, methylene blue.

As used herein, the terms "redox enzyme" refers to an enzyme that can catalyze electron transfer by reduction or oxidation of substrates within a redox reaction. For example, oxidases (e.g. glucose oxidase), reductases, or oxidoreductases.

As used herein, the terms "enzyme cofactor" (i.e. coenzyme), refers to small molecules that carry chemical groups between enzymes. In some embodiments, the enzyme cofactor carries and transfers electrons and functions as an oxidizing or reducing agent in redox reactions. For example, nicotinamide adenine dinucleotide (NADH) or flavin adenine dinucleotide (FADH).

As used herein, the term "capture molecule" refers to a molecule that is capable of binding a reporter molecule, and an electrode. For example, a capture molecule could be a single-stranded DNA (captureDNA) that is complementary to the reporter molecule, or an antigen or an antibody. In other embodiments, the capture molecule comprises an enzyme cofactor and is enzymatically produced to be redox active. In other embodiments, the capture molecule may comprise a redox active molecule. In other embodiments, the capture molecule may comprise a double stranded DNA that is able to recruit a catalytically inactive Cas protein. In this embodiment, either the Cas protein or gRNA can be modified with a redox active molecule or fused to a redox enzyme to create an electrochemical signal.

As used herein, "protein" or "polypeptide", or any protein/polypeptide enzymes described herein, refers to any peptide-linked chain of amino acids, which may comprise any type of modification (e.g., chemical or post-translational modifications such as acetylation, phosphorylation, glycosylation, sulfatation, sumoylation, prenylation, ubiquitination, etc.). For further clarity, protein/polypeptide/enzyme modifications are envisaged so long as the modification does not destroy the desired enzymatic activity.

As used herein, the term "in vitro" refers to activities that take place outside an organism. In some embodiments, "in vitro" refers to activities that occur in the absence of cells.

As used herein, the term "cell-free" a used in "cell-free, detection system" refers to a set of biological components capable of providing for or supporting a biological reaction (e.g., transcription reaction, translation reaction, or both) in vitro in the absence of cells. Cell-free systems can be prepared using proteins, nucleic acid material and other subcellular components either isolated or purified from eukaryotic or prokaryotic cells, including recombinant cells, or prepared as whole extracts or fractions of cells.

As used herein, the term "electrode" refers to any electrode or electrochemical system that is sufficient for detecting the change in electrochemical potential when the reporter molecule specifically binds the capture molecule bound to the electrode. The electrode can be a nanostructured electrode, a non-nano structured electrode, a micro-patterned electrode, or an array thereof.

As used herein, the term "electrochemical signal" refers to the electric potential generated by a chemical messenger. For example, the electric potential generated by the chemical messenger or redox active molecule (e.g. methylene blue) could be measured by an electrode when in close proximity.

As used herein, the term "sample" means any sample comprising or being tested for the presence of one or more target molecule. Samples can include but are not limited to, small molecules, prokaryotic or eukaryotic cell-derived components such as nucleic acid material, proteins, or cellular extracts, extracellular fluid or fluid harvested from the body of a mammal, culture media, blood, plasma, and/or serum thereof.

As used herein, the term "small molecule" refers to a natural or synthetic molecule having a molecular mass of less than about 5 kD. For example, anhydrotetracycline (ATc).

As used herein, the term "transcriptional repressor" refers to a molecule that inhibits transcriptional activity. For example, a transcriptional repressor can be TetR, which binds and inhibits transcription of TetO. ATc may bind TetR and derepress transcription of TetO.

As used herein, the term "transcriptional activator" refers to a molecule that promotes or activates transcriptional activity.

As used herein, the term "computer" refers to an electronic device for storing and processing data, and capable of performing logic functions based on instructions given to it in an adjustable program.

As used herein, the term "portable" refers to a device, such as a computer, that can be held in one or two hands, without the need for any special carriers. In some embodiments, a portable can be used outside of a laboratory setting. In some embodiments, a portable device can be battery powered.

As used herein, the term "multiplex" refers to a system that allows for the simultaneous detection of a plurality of distinct target molecules in a single assay (e.g., at least 2, at least 6, at least 10, at least 20, at least 30 target molecules).

Other objects, advantages and features of the present description will become more apparent upon reading of the following non-restrictive description of specific embodiments thereof, given by way of example only with reference to the accompanying drawings.

DETAILED DESCRIPTION

In one aspect, the present description relates to a direct interface between engineered molecular circuits and electronics. Interfacing in vitro synthetic biology with electronics will enable engineered gene networks to rapidly share data with computational tools, a feature that will drive more sophisticated and interactive diagnostics and embedded sensor applications. Importantly, this electrochemical interface also enables the large-scale multiplexing outputs from molecular circuit-based sensors. Reporter output from these networks has largely been optical, which has limited the potential to measure distinct, parallel signals.

In one aspect, the present description provides an electrochemical interface permitting multiplexed detection for cell-free synthetic gene networks.

In one aspect, the present description provides a scalable system of reporter enzymes that release a modified DNA strand, resulting in recruitment of a redox reporter molecule to the surface of a nanostructured microelectrode and an increase in measured current.

In one aspect, the molecular circuitry system described therein can be used to detect target molecules such as small molecules, DNA, RNA, and proteins, including the detection of multiple antibiotic resistance genes in parallel. This technology has potential for expanding the integration between synthetic biology applications (sensing) and hardware, software, and machine learning.

In one aspect, the molecular circuitry system comprises one or more different switch-based sensors, specific for different target molecules. In some aspects, the switch-based sensor is a toehold RNA switch-based sensor. In some aspects, the target molecule is RNA within a sample and can bind a toehold RNA switch comprising an mRNA sequence encoding a protein. Upon RNA binding, the toehold RNA switch linearizes and the mRNA is translated into said protein. In some aspects, the protein is an activator or is the reporter molecule. In some aspects, the protein is a nuclease. In some aspects, the nuclease is a restriction enzyme. In some aspects, the restriction enzyme is from the list of EcoRV, AciI, ClaI, BanII, BsaAI, BglII, BstEII, HincII, NcoI, or PstI. In some aspects, the nuclease is a Cas protein. In some aspects, the restriction enzyme is specific for a reporter molecule, which is a single stranded DNA strand referred to as reporterDNA. In some aspects, the reporterDNA is inactive when hybridized to a complementary inhibitory single-stranded DNA strand referred to as iDNA. In some aspects, the reporter molecule or reporterDNA comprises a redox active molecule, referred to as a redox active reporter. In some aspects, the restriction enzyme or nuclease specifically cleaves the reporterDNA/iDNA complex, thereby releasing the reporterDNA. In some aspects, a series of electrodes are coupled to a corresponding capture molecule. In some aspects, the capture molecule is a single-stranded DNA strand specific for a reporterDNA. In some aspects, the captureDNA binds the released or active reporterDNA. In some aspects, an electrode detects an electrochemical signal generated by the electric potential of the redox active molecule that is bound to the reporterDNA. In other aspects, the activator or the reporter molecule comprises enzyme that could any oxidase, reductase, or oxidoreductase. In some aspects, the reporter molecule or reporterDNA comprises an enzyme cofactor. In some aspects, the enzyme produces a redox active reporter. In some aspects, the oxidase, reductase, or oxidoreductase enzymes are fused to Cas protein and recruited to the capture molecule on the surface. In other aspects, the RNA toehold switch encodes an RNAzyme.

In one aspect, the target molecule is DNA within a sample and can bind a toehold DNA switch comprising a DNA sequence encoding an mRNA, gRNA, or RNAzyme. In some aspects, the mRNA is translated into a protein, which can be the reporter molecule or an activator that activates a reporter molecule. In other aspects, the transcribed gRNA is bound by a Cas protein, which can activate a reporter molecule. In other aspects, the DNA sequence encodes a DNAzyme, that can activate a reporter molecule.

In one aspect, the target molecule is RNA within a sample and can bind a riboregulated toehold-gated guide RNA (gRNA) switch-based sensor. In some aspects, the gRNA is exposed and can be bound by a Cas protein. In some aspects, the gRNA is specific for a reporterDNA. In some aspects, the Cas-gRNA complex binds and cleaves the reporterDNA/iDNA complex, thereby releasing and activating the reporterDNA.

In one aspect, aptamer switch-based sensors detect certain target molecules within a sample. In some aspects, the aptamer switches detect specific molecules like proteins or small molecules. In some aspects, the aptamer is DNA-based. In other aspects, the aptamer is RNA-based. In some aspects, the aptamer is fused to a DNA or RNA sequence. In some aspects, upon aptamer binding of a specific molecule, DNA can be transcribed into an RNA sequence, which could be an mRNA, gRNA, or RNAzyme. In some aspects, the mRNA is be translated into a protein, which is the reporter molecule or is an activator that can activate a reporter molecule. In other aspects, the transcribed gRNA is bound by a Cas protein, which can activate a reporter molecule. In other aspects, the DNA sequence encodes a DNAzyme, that can activate a reporter molecule.

In one aspect, the target molecule is small molecule within a sample and can activate an inducible transcription system by binding a transcriptional activator or transcriptional repressor. In some aspects, the inducible transcription system encodes an mRNA, gRNA, or RNAzyme. In some aspects, the mRNA is translated into a protein, which is the reporter molecule or is an activator that can activate a reporter molecule. In other aspects, the transcribed gRNA is bound by a Cas protein, which can activate a reporter molecule. In other aspects, transcribed gRNA is not bound to Cas protein in its inactive state (e.g. riboregulated guide RNAs); however, upon activation by target sequence (e.g. pathogen RNA) the gRNA becomes available to bind to the Cas protein and generate an electrochemical signal.

In one aspect, by amalgamating programmable molecular circuit-based sensors with electrochemical detection, the molecular circuitry system as described herein is adaptive, broadly capable and has the potential to allow 5-10 multiplexed sensors to operate with parallel but distinct signals.

In some aspects, the electrode-bound capture molecule is coupled to an enzyme cofactor. In some aspects, the activator/reporter molecule comprises an enzyme that could be any oxidase, reductase, or oxidoreductase and can produce a redox active capture molecule. In other aspects, the redox active reporter molecule continuously produces an electrochemical signal detected by the electrode. In some aspects, the activator/reporter molecule that is an enzyme can inhibit the detection of the electrochemical signal by the electrode.

In one aspect, the electrode-bound capture molecule could be an aptamer DNA or RNA and is coupled to a redox active molecule. In some aspects, the electrochemical signal is continuously detected by the electrode. In some aspects, the reporter molecule/activator can bind the aptamer and inhibit detection of the electrochemical signal.

Using DNA-functionalized nanostructured microelectrodes as electrochemical detectors (26,32), the activation of molecular circuits is linked to specifically paired electrodes through the expression of orthogonal reporters (see FIG. 1). Sequence-specific and scalable, this approach uses the production of restriction enzyme-based reporters to catalyze the release of methylene blue-labelled ssDNA (reporterDNA), which in turn interacts with complementary ssDNA (captureDNA) conjugated to the electrode surface. Upon hybridization of reporterDNA with captureDNA, methylene blue, a redox reporter molecule, is brought in close proximity to the electrode surface, allowing for a large increase in the measured current at that electrode (22,27). It is this conversion of molecular circuit-based sensor activation into sequence-specific DNA interactions that enables distinct and multiplexed signals to operate without crosstalk. Here, we demonstrate the power of this new electrochemical interface by detecting the activation of rationally designed toehold-switch-based RNA sensors, a small-molecule actuated synthetic gene network and demonstrate the multiplexed detection of colistin antibiotic resistance genes.

In one aspect, upon activation of the upstream system by a target molecule, nanostructured microelectrodes recruit the reporter molecule to their surface (e.g. redox-active reporterDNA through complementary binding to captureDNA), generating an electrochemical signal. Each sensor system is engineered to produce a unique activator or reporter molecule (e.g. nuclease with sequence-specific cleavage activity that is coupled to a distinct reporter system and capture molecule (e.g. reporter DNA molecule specific—capture DNA pair) for multiplexed signaling.

In one aspect, the detected electrochemical signals, or change thereof, by the electrodes are transmitted to a processing device, such as a computer. In some aspects, the signals are analyzed by computer-implemented methods such as software. In some aspects, the signals are converted into rich data sets, that may also be used for machine learning applications.

Taken together, the present description provides a series of proof-of-concept experiments for a direct and scalable interface between engineered molecular circuits and electronics. Interfacing cell-free synthetic biology with electronics will enable engineered gene networks to curate mixed molecular information and rapidly share data with computational tools, a capability that promises to drive more sophisticated and interactive applications. Potential uses include high-content multiplexing systems for decentralized sensing in health, agriculture, national security and industry, among others. Using low-cost electronics, ultimately, we envision this interface to enable dozens of diagnostics to operate for the cost of a single test in our current colorimetric format (<$1/test) (15). Moreover, by simply modifying the upstream molecular sensor elements in the system, the same reporter enzyme-electrode pairs can be left unchanged, along with common microelectrode hardware, to, in principle, serve any sensor application. Toehold switches can be rationally designed (35) and therefore the platform can be tailored to detect virtually any nucleic acid sequence. The stable and biosafe nature of the cell-free format also means that the technology can be used without the limitations of cellular systems, potentially enabling new applications and operating environments outside of the laboratory.

This approach also holds exciting technical implications for the field of synthetic biology. First, this work highlights the potential for chemistry to enable and mediate signaling for synthetic gene networks, creating a much-needed mechanism for increasing the bandwidth of sensor outputs. This contrasts with conventional reporters, which are optical and have a limited capacity for multiplexing (9,15). While sensing arrays can be contemplated for optical detection (e.g. microarrays), the complexity of these devices and the optics needed for detection are major disadvantages. Second, tackling another key challenge in the field, here we demonstrate that rather than having to encode decision making and memory features genetically into molecular circuits, we can off-load these features to attached electronics. The system continues to take advantage of biology's incredible capacity to sense, but has the potential to dramatically reduce the time needed to develop synthetic biology applications. With this approach, the underlying connectivity of sensory outputs can be re-programmed at will, easily creating any number of logic calculations (e.g. AND gates, etc.) by simply modifying the code at the level of the software rather than at the level of the DNA. Looking forward, we see this bio-electrochemical approach as providing the field a new enabling venue and one that provides new opportunities for even greater interdisciplinarity and rational design of chemical and biological systems.

EXAMPLES

Example 1: Materials and Methods 1.1 Chip Fabrication

Microelectrode patterns including reference, counter, and working electrodes were generated using standard contact photolithography techniques from glass substrates layered with chrome, gold, and with or without positive photoresist (AZ1600) obtained from Telic Company or EMF. The working electrodes were nanostructured using electrodeposition in solution of 50 mM $AuCl_3$ in 0.5 M HCl. Standard three-electrode system with an Ag/AgCl reference electrode and a platinum counter electrode was set up at constant potential of 0 mV for 100 s using Bioanalytical Systems Epsilon potentiostat (West Lafayette, IN, USA). Finally, 100 μm high PDMS channels were fabricated and bonded to chips using standard soft lithography techniques.

1.2 CaptureDNA Deposition

CaptureDNA strands were obtained from Integrated DNA Technologies containing a 6-carbon linker with a terminal thiol. Final concentrations of 10.5 μM of captureDNA along with 5 μM mercaptohexanol (MCH) were deposited on nanostructured working electrodes, and incubated in a humid environment at room temperature for approximately 14 hr. In order to deposit multiple DNA capture strands on a single chip, Dowsil™ 3145 RTV silicone adhesive sealant (Dowsil, Midland, Michigan, USA) was used to create separate chambers for DNA deposition, and the glue was removed after overnight incubation with the DNA solutions. Chips were then washed 3× with 1×PBS. A solution of 1 mM MCH was added to cover the working electrodes of each chip to backfill any gold surface and prevent nonspecific interaction. After incubation for 3 hr at room temperature, chips were washed 3× with 1× Phosphate-Buffered Saline, pH 7.4 (PBS), then rinsed with ddH2O and dried under a stream of $N_2$.

1.3 Reporter DNA Preparation

ReporterDNA was ordered from Integrated DNA Technologies with a terminal amine, which was used for labeling with a methylene blue NHS Ester (Glen Research, Sterling, VA, USA) according to manufacturer's protocol. Labeled DNA was then purified using reverse phase HPLC, dried via lyophilization, and re-dissolved in 1×PBS. Then reporter and inhibitor DNA strands were annealed at ratio of 1:4 (for initial proof-of-concept experiments) or 1:10 (for multiplexed experiments) in 1×PBS incubated at 95° C. for 4 min. The solutions were then cooled slowly to room temperature.

1.5 Cell-Free Expression of Restriction Enzymes

All experiments were performed using the recombinant cell-free protein expression system (CFS), PURExpress™ (E6800S, NEB, Ipswich, MA, USA) following manufacturers procedures with an additional 0.5% by volume RNAse inhibitor (M0314S, NEB). All DNA constructs and gene-circuits were designed to be compatible with this cell-free system. Restriction enzyme expression reactions were assembled using 10 nM linear DNA encoding for the restriction enzyme in CFS. To measure restriction enzyme expression and activity electrochemically, the reporterDNA-iDNA complex was added to a final concentration of 100-280 nM reporterDNA. If measurements were to be made in real-time, the solution was then added directly to the electrochemical chips for measurement during incubation at 37° C. Unless otherwise stated, the reactions were incubated at 37° C. for 1 hr before addition to chips. The reactions were then incubated on the chips for 15-30 min at 37° C. before electrochemical measurements were obtained.

Figure 5A:
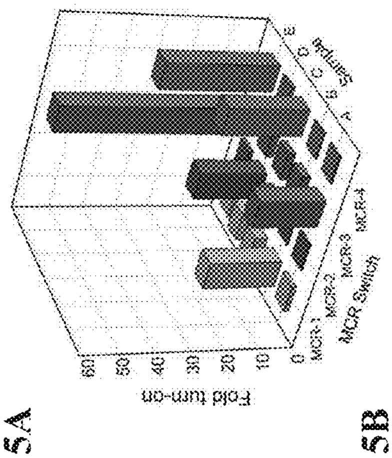
FIG. 5A: Detection of Mobilized Colistin Resistance (MCR) genes. Toehold switch-based RNA sensors were designed and screened for the detection of four MCR genes. Five separate experiments were performed on-chip in the presence of all components except the corresponding MCR-specific trigger RNA(s). The first four experiments (samples A-D) test the detection of single MCR-related RNAs (1 nM) based on the electrochemical response (Sample A: MCR-3 RNA trigger, Sample B: MCR-1 RNA trigger, Sample C: MCR-4 trigger and Sample D: MCR-2 trigger). Sample E tests the co-detection of MCR-3 and MCR-4 RNA triggers (1 nM each) in parallel. Data was normalized to the measured current in the absence of trigger RNA (5 μM). S refers to toehold switch, T refers to the corresponding trigger RNA. Graphs represent peak current for methylene blue. Data represents the mean±SE of three replicates.

For the restriction enzyme co-expression experiments, we took advantage of the methyl sensitivity of AciI, BsaAI, and HincII. The coding DNA sequences for AciI, ClaI, and EcoRV were methylated to protect against cross cleavage by, BsaAI/HincII, BsaAI, and AciI respectively by combining 10 units of CpG methyltransferase (#M0226M, NEB) with 4 μg of linear DNA at 37° C. overnight in 100 μl 1× NEBuffer™ 2 (NEB). The methylated product was purified using QIAquick™ Spin Columns (#28104, Qiagen, Germantown, Maryland, USA). 30 nM of either methylated (AciI, ClaI, EcoRV) or non-methylated (BsaAI, HincII) coding sequences were used for co-expression and results monitored electrochemically as described above (FIG. 3H). RNA MCR switches with concentrations of 200 nM MCR1-EcoRV, 25 nM MCR2-AciI, 250 nM MCR3-BanII, and 100 nM MCR4-ClaI were used for multiplexed electrochemical experiments. Here, final concentrations of 1 nM RNA trigger sequences and 100 nM reporterDNA were also added to the CFS (FIG. 5A).

1.6 Electrochemical Measurements

All measurements were performed using either a Bioanalytical Systems Epsilon potentiostat or a PalmSens PSTrace™ potentiostat, both with a three-electrode system. An on-board gold reference electrode was used in addition to a platinum wire auxiliary electrode. The multiplex chip was designed to house both an on-board gold reference and counter electrodes. Square wave voltammetry (SW) signals were obtained with a potential pulse step of 1 mV at a frequency of 60 Hz and an amplitude of 25 mV, with measurements taken from 100 to 450 mV.

Figure 4A:
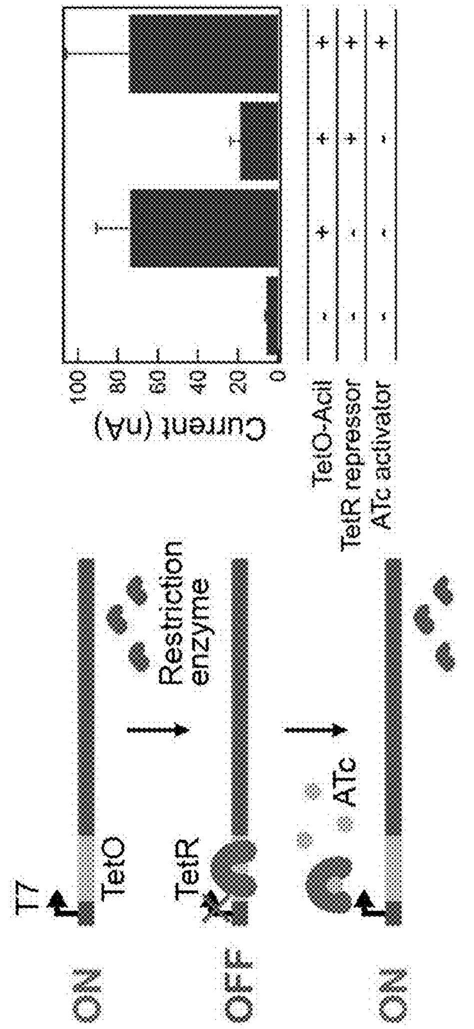
FIG. 4A: Application of the gene-circuit electrochemical interface for small molecule- and RNA-actuated electrochemical signaling. Anhydrotetracycline (ATc)-mediated derepression of TetR-regulated TetO expression of the restriction enzyme-based reporter AciI (left). ATc-dependent induction (440 μM) of electrochemical signaling on-chip (right).
Figure 4B:
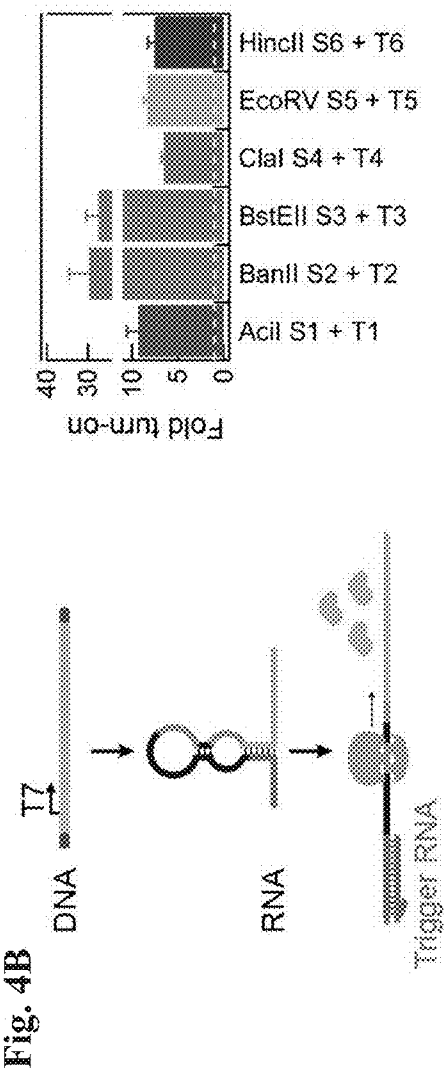

1.7 Toehold Switch-Based Design and Multiplexed Sensing of MCR Antibiotic Resistances A series of toehold switches recognizing synthetic target sequences were used to build toehold-based gene-circuits14 (Table 3). Briefly, each toehold switch was constructed separately with multiple restriction enzymes by overlap extension PCR using the primers. For each construct, both the toehold switch sequence and reporter enzyme were amplified with PCR primers to add ~20 nucleotides that overlap between the two sequences. The overlapping region allows for attachment of the switch to reporter in the second round of PCR using forward and reverse primers. The activity of these toehold switch-based sensors was tested and screened for performance using MB fluorescence assays as described above. Top performing switches were then tested using electrochemical assays. Here reactions for restriction enzyme expression were assembled as described previously in CFS, containing 10 nM linear DNA coding for the respective restriction enzyme under switch-molecular circuit control and 1 μM trigger RNA. Reactions were incubated at 37° C. for 1 hr before adding to electrochemical detection chips, where they were then incubated for 20-60 min before measuring current (FIG. 4B). Trigger RNA was produced in vitro using HiScribe™ T7 High Yield RNA Synthesis Kit (E2040S, NEB).

Figure 5B:
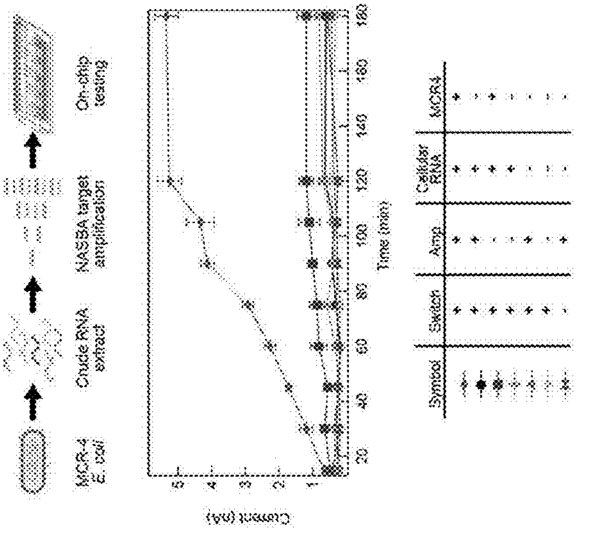
FIG. 5B: On-chip electrochemical signaling from activation of MCR-4_ClaI in the presence of MCR-4 RNA from complex whole cell RNA samples isolated from *E. coli*. Tested with a combination of inputs, the real-time signal is only detected in the presence of MCR-4 RNA and isothermal amplification. Cellular RNA was isolated from Dh5α *E. coli* cells in the presence or absence of a plasmid expressing MCR-4. All electrochemical measurements were performed with square wave voltammetry and peak current is used for calculation of fold turn-on. Switch, MCR-4_ClaI; Amp, NASBA with primers (+) or without primers (−). Data represents the mean±SE of three replicates.
Figures 6A, 6B, 6C, 6D, 6E:
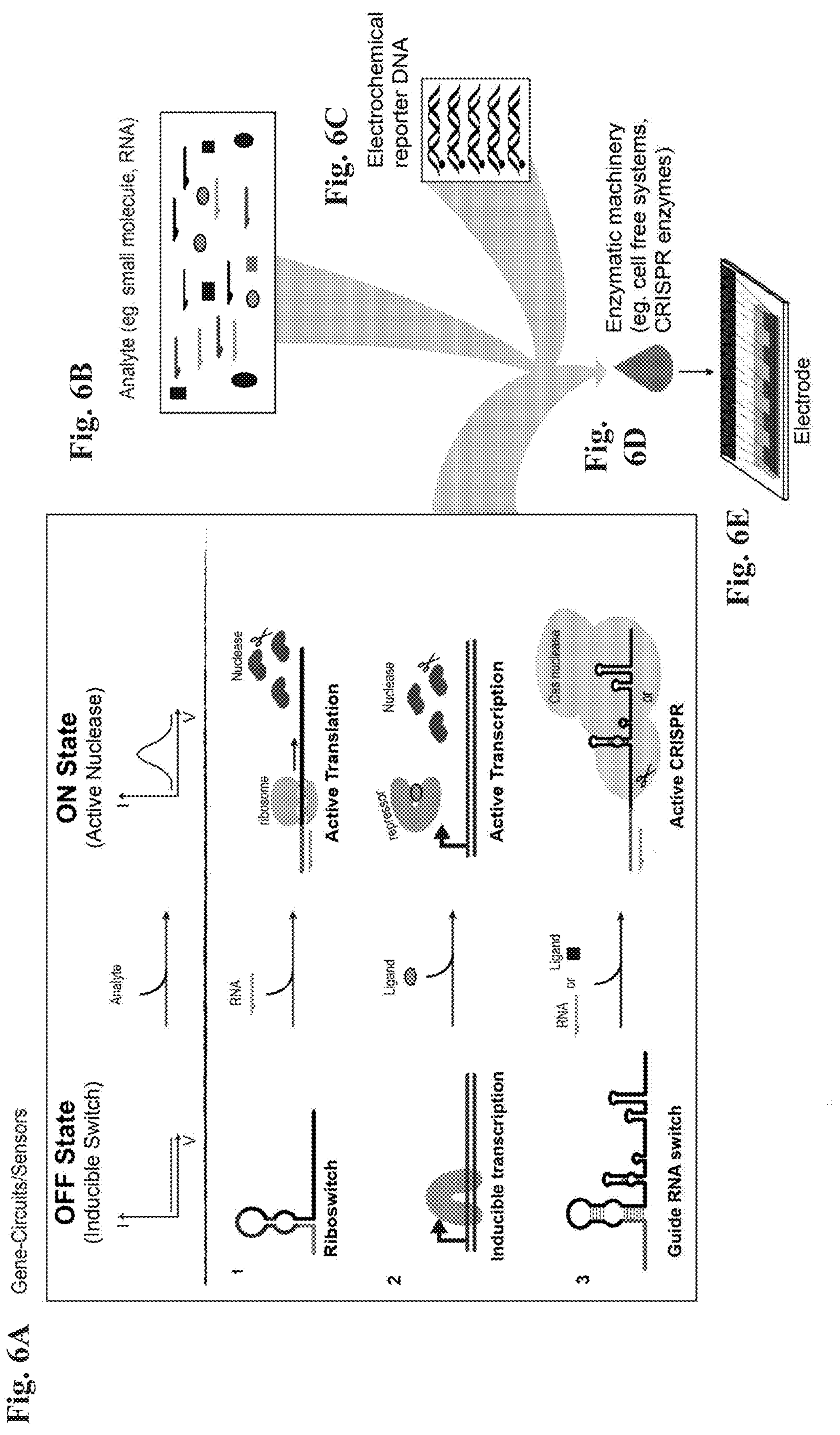
FIG. 6A. A direct molecular circuit-electrode interface as novel method for sensor outputs. The system comprises five main components Molecular circuit-based sensors which can include riboswitches, inducible transcription or guide RNA-based mechanisms. Upon activation of the sensors, these molecular circuits generate a nuclease-based reporter.
FIG. 6B The target analyte of interest (e.g. RNA, DNA, small molecule) that is sensed by the molecular circuit-based sensor.
FIG. 6C ReporterDNAs, which are the substrates of the nucleases generated by the sensors FIG. 6D The cell-free biochemical system that provides the necessary transcription and translation activity.
FIG. 6E The electrode array chip which is used to host the captureDNA and measure the electrochemical response to binding of released reporterDNAs. Schematics represent various types of gene-circuits capable of sensing analytes such as nucleic acids and small molecules. First, gene-circuits can be designed to regulate translation of nucleases such as restriction enzymes using riboswitches (e.g. toehold switch) upon sensing specific target RNA analytes. Secondly, gene-circuits can also be designed to regulate expression of nucleases at the transcription level. The example represented here uses a transcriptional repressor that can depart and allow for proper transcription of specific nucleases in presence of a specific ligand (e.g. Tet repressor). Thirdly, CRISPR machinery can be used in combination with inducible guide RNAs that can be activated by either small molecule ligands[3] or specific RNA sequences[4] and guide Cas mediated cleavage in sequence specific manner.

For proof of concept experiments (FIG. 4B) cell-free reactions were set up as described above supplied with 10 nM DNA toehold switches. For multiplexed MCR detection, switches were supplied as RNA, with concentrations of 200 nM MCR-1_EcoRV, 25 nM MCR-2_AciI, 250 nM MCR-3_BanII, and 100 nM MCR-4_ClaI. Respective switches were triggered by 1 nM RNA trigger sequences in presence of 100 nM reporterDNA (FIG. 5B).

Example 2: Screening for High-Performing Restriction Enzyme-Based Reporters

Figure 2A:
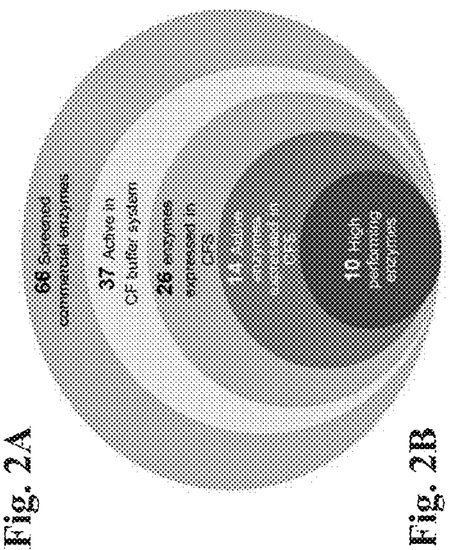
FIG. 2A: Development of orthogonal, restriction enzyme-based reporters. Candidate restriction enzymes were evaluated through a four-step screening pipeline (i-iv) designed to find enzymes with high rates of expression and processivity in the cell-free expression system (CFS). i) 37 of 66 commercially available enzymes were active in the cell-free (CF) buffer system that replicates the pH, buffer and salt composition found in the complete transcription and translation system, ii) 26 of the 37 above restriction enzymes were successfully expressed de novo in the cell-free system, iii) 14 of these 26 cell-free expressed enzymes showed high levels of cleavage activity, iv) 10 of the 14 enzymes demonstrated high rates of enzyme-mediated cleavage from de novo cell-free expression.
Figure 2B:
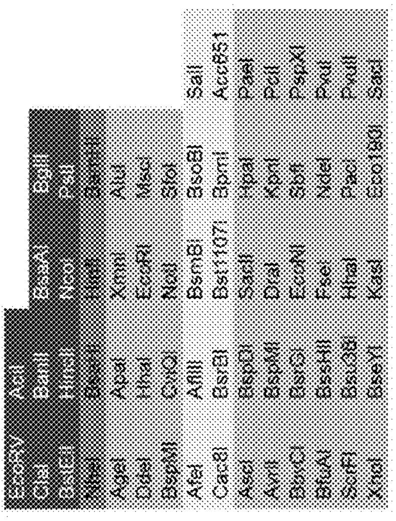
FIG. 2B: A summary of the performance for screened restriction enzymes with colors matching the categories described in FIG. 2A. Representative data of three candidate restriction enzyme-based reporters in molecular beacon cleavage assays. Data presented as percent of maximum fluorescence for each molecular beacon, error bars represent SE (N=3).

The creation of this electrochemical approach to gene circuit-based sensor signaling required that we first identify a set of restriction enzymes capable of rapid and robust performance. We screened 66 commercially available restriction enzymes for cleavage activity under buffer conditions required for the cell-free transcription and translation system (FIG. 2A, B) (11). The ability of restriction enzymes to cleave target DNA was evaluated using gel electrophoresis. The commercially available PURExpress cell-free system (NEB) was selected for experiments because of its recombinant nature, meaning that it is free from background nuclease activity. Of the 37 restriction enzymes that were capable of cleavage, DNA sequences encoding for 26 restriction enzymes were designed and proteins were successfully expressed upon transcription by T7 RNA polymerase (RNAP) in the cell-free system (Table 1) After a three-hour expression period, restriction enzyme activity was tested using gel-electrophoresis-based analysis.

Figure 2C:
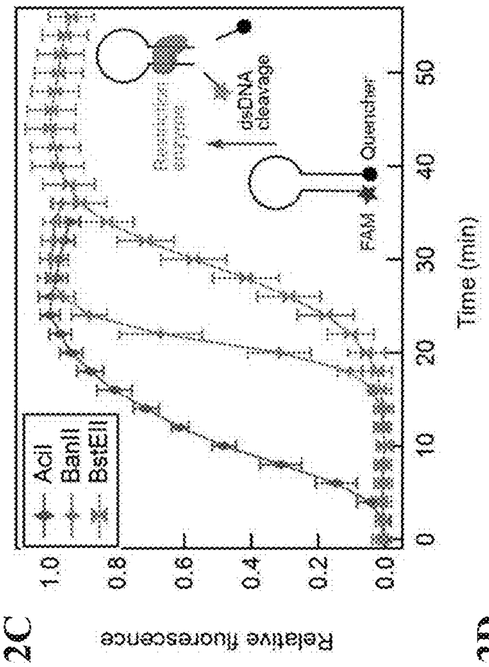
FIG. 2C: Heat map of specific enzyme activity. All combinations of restriction enzymes and molecular beacons were tested. Values are average of triplicates at 180 min.
Figure 2D:
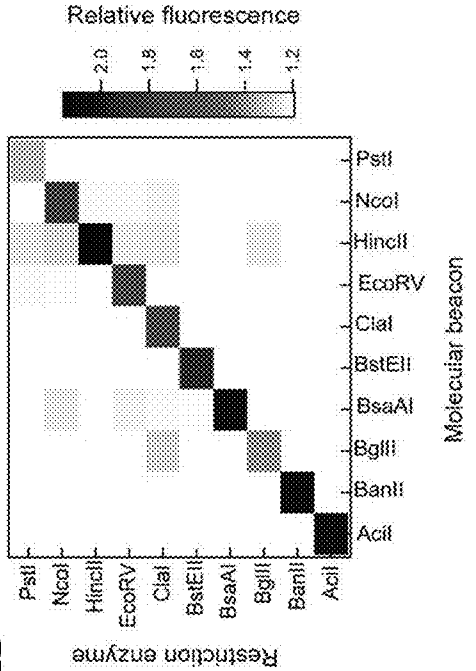
FIG. 2D: Expression analysis of each restriction enzymes in the presence of all ten respective molecular beacons individually.

Given that restriction enzyme expression and processivity are critical for reporter performance, we developed a fluorescence-based molecular beacon assay to monitor DNA cleavage in real-time as the restriction enzymes were expressed in vitro. The hairpin-based molecular beacons contain a DNA recognition site for each of the respective restriction enzymes and are designed with a 5' FAM-6 fluorophore and a 3' BHQ-1 quencher (FIG. 2C) (33). Upon restriction-enzyme-mediated cleavage, the FAM-6 fluorophore is released, allowing for tracking of enzyme activity over time. De novo expression of candidate restriction enzymes resulted in significant cleavage activity by six restriction enzymes as early as fifteen minutes (AciI, BanII, BsaAI, BstEII, ClaI, EcoRV) and by others at later time points (HincII, BglII, NcoI, PstI). The orthogonality of these ten restriction enzymes was then tested by expressing each enzyme in the presence of all ten respective molecular beacons individually. Results indicated good orthogonality, with little crosstalk between restriction enzymes (FIG. 2D).

Figures 3A, 3B, 3C, 3D, 3E, 3F, 3G, 3H:
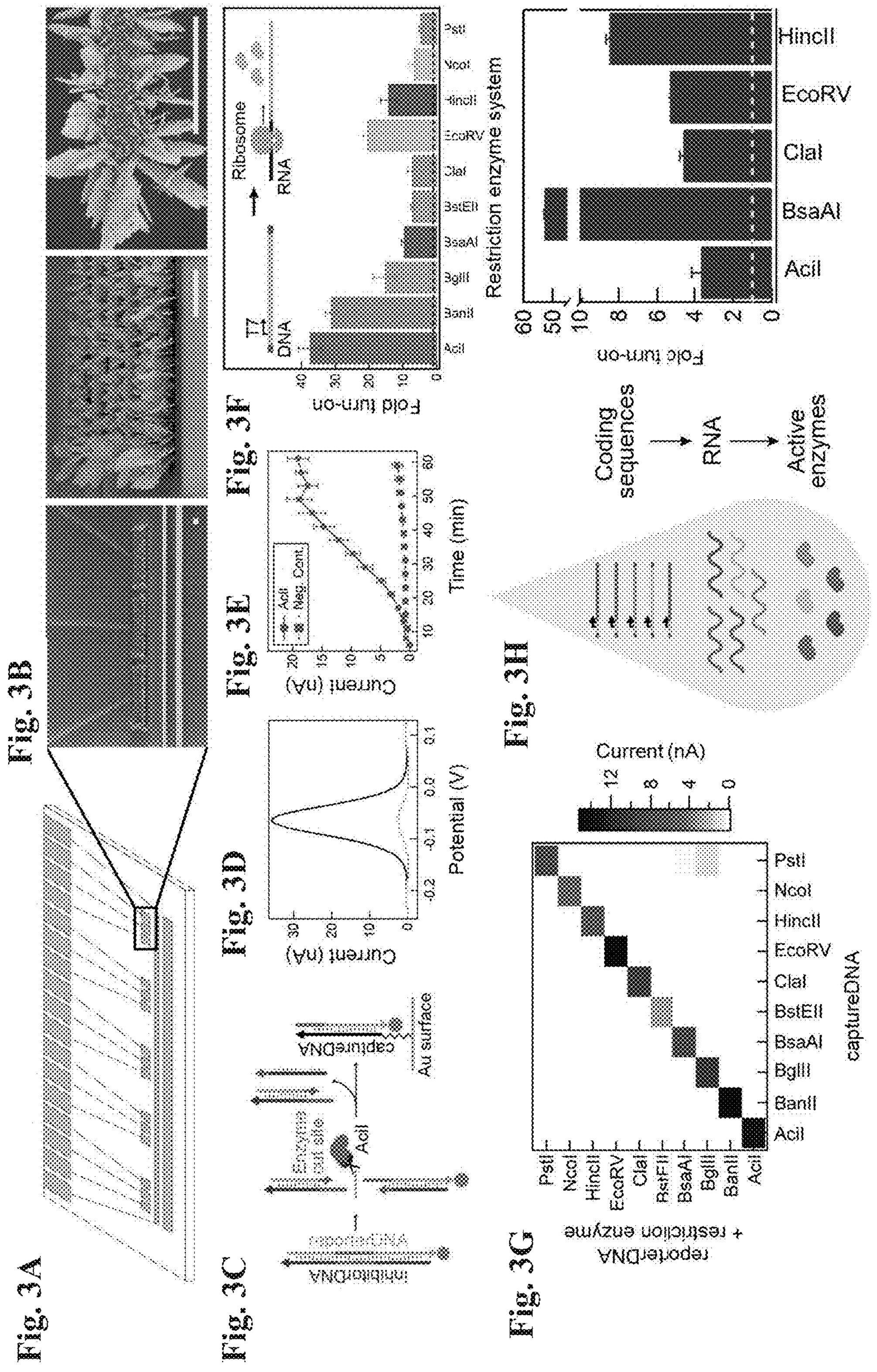

Example 3: Electrochemical Detection of Restriction Enzyme-Activated Redox Reporters With a set of restriction enzymes established, we next developed the companion electrode and redox reporter systems. Each chip contains an array of fifteen micropatterned electrodes arranged in five sets of three, which were prepared using standard photolithography techniques (FIG. 3A, B). Briefly, gold electrodes were patterned on a glass wafer, followed by a layer of photoresist, to create six 400 μm×20 μm openings over each electrode and to prevent nonspecific interactions. Electrodeposition in a gold chloride solution was then employed to create nanostructured microelectrode topologies, which were found to provide optimal speed of detection and sensitivity (34). Nanostructured electrodes were tested over time and found to perform stably, with little decrease in current, when stored under ambient atmosphere, humidity and temperature. After electrode preparation, captureDNA complementary to the reporterDNA for each restriction enzyme was conjugated to each of the five triplicate electrode sets via a terminal thiol group; 6-mercaptohexanol (MCH) was added as a co-adsorbent to minimize electrostatic repulsion on the electrode surface (Table 2).

Release of the complementary reporterDNA is catalyzed by restriction enzyme-dependent cleavage of free-floating DNA duplexes in cell-free reactions (FIG. 3C). These stable DNA duplexes are comprised of a full-length reporterDNA strand and a complementary inhibitor DNA strand (iDNA), which prevents interaction with electrodes in the absence of cleavage. Conversely, upon duplex cleavage, the truncated reporterDNA is designed to hybridize with captureDNA and bring the terminal methylene blue label to the electrode surface, enabling electron transfer to create a restriction enzyme-dependent electrochemical signal (FIG. 3D). The preference of the truncated reporterDNA for the captureDNA is driven by mismatched base pairing with the iDNA, which leads to greater relative stability (higher melting temperature, AG) when hybridized to on-chip captureDNA. As in the molecular beacon assay, restriction enzyme specificity results from recognition of sequence-specific DNA cleavage sites, and electrochemical detection requires conjugation of the complementary captureDNA on the electrode surface.

Using T7-RNAP expression, we showed that the restriction enzyme-mediated electrochemical signal can be detected in as little as 20 minutes after transcription initiation using square wave voltammetry (FIG. 3E). We next determined that this model of restriction enzyme-mediated signaling is scalable with the demonstration of ten restriction enzyme-electrode pairs (FIG. 3F). Here expression constructs for each restriction enzyme were combined in cell-free reactions with their respective reporterDNA duplexes (reporter DNA-iDNA) and electrodes containing one of the ten captureDNA strands. After a 1 hour off-chip reaction incubation at 37° C., all ten pairs led to significant electrochemical signal fold change at 30 minutes once applied to the electrodes. The orthogonality of all ten restriction enzymes was then tested by repeating the expression of each enzyme in the presence of all ten reporterDNA duplexes individually. The resulting electrochemical signaling demonstrated strong orthogonality and little crosstalk (FIG. 3G). A subset of these restriction enzymes could also be co-expressed in a single reaction mixture to generate clear electrochemical signals on chip. In this experimental set-up, all five restriction enzyme expression constructs and their corresponding reporterDNA duplexes were combined in a single cell-free reaction volume (FIG. 3H, left). When expressing multiple restriction enzymes in a single pot, it is important to ensure that enzymes are not cross-reactive towards the DNA encoding the respective restriction enzymes. To address this, restriction enzyme expression here was performed using methylated DNA to prevent restriction enzyme-mediated cleavage, (FIG. 3H) and, alternatively, by modifying their DNA sequences to remove restriction enzyme cleavage sites. These strategies effectively limited cross-reactivity and broaden the pool of restriction enzymes that could be used as reporters. With reporter validation complete, we now refer to these restriction enzymes simply as reporter enzymes.

Example 4: Electrochemical Detection of Molecular Circuit-Driven Expression: TetO and Toehold Switches With the fundamental components for the electrochemical interface complete, we next developed applications to demonstrate electronic sensing of molecular circuit activation. We began with TetO-regulated expression of a reporter enzyme (FIG. 4A). TetO is a 19 bp operon sequence that can be placed between a promoter and an upstream (5') of a gene of interest to provide tetracycline-responsive expression. In this system, transcription is regulated through Tet repressor (TetR) binding to the T7-TetO promoter region, which inhibits transcription, and the small molecule tetracycline analog anhydrotetrcycline (ATc), which relieves this inhibition (FIG. 4A, left). By placing the reporter enzyme AciI under TetO regulation, we were able to demonstrate the corresponding activation and inhibition of electrochemical signaling in the presence and absence of Atc, respectively (FIG. 4A, right). These signals corresponded closely with positive and negative controls.

The multiplexed linkage of molecular circuits to electronics has the potential to enable automated and high-capacity biosensing. We have previously demonstrated that toehold switches can be designed to recognize specific RNA sequences and that these RNA sensors can be used to identify the presence of pathogens (14,15). To explore the potential of multiplexing such sensing capacity, we used six toehold switches designed to recognize six synthetic model sequences (Table 3) (35). Cell-free reactions containing a toehold switch, with or without its respective RNA trigger sequence, were monitored electrochemically at 37° C. on microelectrode arrays containing the complementary captureDNA and free floating reporterDNA duplex. This resulted in the sequence-specific RNA activation of toehold switches and electrochemical outputs that ranged from 7- to 30-fold (FIG. 4B) compared to background. The fold change values represent maximum signal between 60 and 90 minutes, with significant signals observable in as little as 15-20 minutes. Importantly, as previously demonstrated (14, 35), the performance of riboregulators is switch-dependent, and here we show that this signal can also be modulated by the choice of reporter enzyme, providing a further layer of engineering control.

Example 5: Application to Detection of Colistin Antibiotic Resistance Genes

The overuse of antibiotics has given rise to the growing threat of drug resistance. With the vast majority of antibiotic use related to agricultural settings, farms represent a significant risk for the emergence of resistance (36,37). Here we developed toehold switch-based sensors specific to the coding regions of resistance genes for the key last-line antibiotic colistin (MCR-1, MCR-2, MCR-3 and MCR-4). These genes have recently been identified in livestock globally and represent a dangerous threat to the efficacy of an antibiotic of last resort.

Using a purpose-built algorithm for toehold switch design (15), each MCR gene was computationally screened for regions of low structural complexity that could be targeted by toehold switches. We then synthesized toehold switch designs complementary to the 24 top ranked binding sites within each MCR gene and ligated a unique reporter enzyme gene to each set of switches (MCR-1_EcoRV, MCR-2_AciI, MCR-3_BanII, MCR-4_ClaI). Reporter enzyme selection was based on the speed of DNA cleavage in time course assays (FIG. 2C). The performance of the resulting 96 sensors was then screened against their respective RNA sequences for optimal ON/OFF ratios using molecular beacons. Top performing sensors were then validated on microelectrode arrays. With the activity of each MCR sensor linked to a unique reporter enzyme, we first demonstrated that the corresponding electrode array for all four MCR genes can detect each gene independently (FIG. 5A, samples A-D). Each of the MCR RNAs (1 nM, samples A-D) were added to four cell-free reactions each containing one set of the toehold sensors (MCR-1_EcoRV, MCR-2_AciI, MCR-3_BanII, MCR-4_ClaI) and corresponding reporterDNAs, and incubated for 30 minutes off-chip at 37° C. After separate incubation, the four reactions were pooled together on-chip (e.g. samples A, B, C and D) for incubation at 37° C. The electrochemical response for each of the four MCR genes individually provided a clear signal enhancement of ~20-fold (50 min). We then demonstrated that this capacity could be multiplexed, enabling the specific and simultaneous detection of RNA sequences from MCR-3 and MCR-4 (FIG. 5A).

As with other cell-free sensors (15,20), we next used isothermal amplification (1 hour) to specifically amplify target sequences before adding the sample to cell-free reactions containing toehold sensors. The limit of detection (LOD) without an amplification step was determined through on-chip sensing of MCR-1 at RNA concentrations between 10 nM and 150 nM using 200 nM MCR-1_EcoRV switch following the experimental design described above. These measurements yielded a calculated LOD of 64.5 nM. With the addition of a Nucleic Acid Sequence Based Amplification (NASBA) step upstream of the electrochemical workflow, we were able to extend the detection of the antibiotic resistance gene MCR-4 to the low femtomolar range (1 fM), an improvement of many orders of magnitude (~107). In these experiments, MCR-4 RNA at 1 fM was added to a NASBA reaction (1 hr) and this amplified RNA was then added to cell-free reactions at 14% of total cell-free reaction volume. Here the combined workflow led to a robust increase in electrochemical signal on-chip after 120 minutes of incubation at 37° C. This level of performance compares well with the turnaround time and sensitivity of other recently published cell-free synthetic biology-based detection schemes (2-3 hours) (15,38).

Finally, with a long-term goal of applying this approach to the interrogation of real-world samples, we wanted to determine the capacity of our on-chip detection for more complex samples. Here the MCR-4 gene was expressed in *E. coli* and then total RNA was collected from the resulting culture. In total, cellular RNA was added to the NASBA reaction (1 hr) at concentration of 30 ng/μl for isothermal amplification using MCR-4 specific primers. The amplified MCR-4 mix was added without purification to the cell-free reactions containing (MCR-4_ClaI switch), followed by 30 minutes of off-chip, and 15 minutes of on-chip incubation at 37° C. prior to taking the first electrochemical measurement (FIG. 5B). Electrochemical activation of the system was specific to MCR-4 RNA in the presence of high background off-target RNA sequences and provided a strong, distinct signal against negative controls.

REFERENCES

1. Cameron, D. E., Bashor, C. J. & Collins, J. J. A brief history of synthetic biology. Nat. Rev. Microbiol. 12, 381-90 (2014).
2. Cheng, A. A. & Lu, T. K. Synthetic biology: an emerging engineering discipline. Annu. Rev. Biomed. Eng. 14, 155-78 (2012).
3. Fossati, E. et al. Reconstitution of a 10-gene pathway for synthesis of the plant alkaloid dihydrosanguinarine in *Saccharomyces cerevisiae*. Nat. Commun. 5, 3283 (2014).
4. Smanski, M. J. et al. Synthetic biology to access and expand nature's chemical diversity. Nat. Rev. Microbiol. 14, 135-49 (2016).
5. Green, A. A. et al. Complex cellular logic computation using ribocomputing devices. Nature 548, 117-121 (2017).
6. Yehl, K. & Lu, T. Scaling Computation and Memory in Living Cells. Curr. Opin. Biomed. Eng. 4, 143-151 (2017).
7. Kitada, T., DiAndreth, B., Teague, B. & Weiss, R. Programming gene and engineered-cell therapies with synthetic biology. Science 359, eaad1067 (2018).
8. Mao, N., Cubillos-Ruiz, A., Cameron, D. E. & Collins, J. J. Probiotic strains detect and suppress cholera in mice. Sci. Transl. Med. 10, eaao2586 (2018).
9. Kotula, J. W. et al. Programmable bacteria detect and record an environmental signal in the mammalian gut. Proc. Natl. Acad. Sci. U.S.A. 111, 4838-43 (2014).
10. Keasling, J. D. Synthetic biology and the development of tools for metabolic engineering. Metab. Eng. 14, 189-95 (2012).
11. Shimizu, Y. et al. Cell-free translation reconstituted with purified components. Nat. Biotechnol. 19, 751-755 (2001).
12. Jewett, M. C., Calhoun, K. A., Voloshin, A., Wuu, J. J. & Swartz, J. R. An integrated cell-free metabolic platform for protein production and synthetic biology. Mol. Syst. Biol. 4, 220 (2008).

13. Shin, J., Jardine, P. & Noireaux, V. Genome replication, synthesis, and assembly of the bacteriophage T7 in a single cell-free reaction. ACS Synth. Biol. 1, 408-413 (2012).
14. Pardee, K. et al. Paper-based synthetic gene networks. Cell 159, 940-954 (2014).
15. Pardee, K. et al. Rapid, Low-Cost Detection of Zika Virus Using Programmable Biomolecular Components. Cell 165, 1255-1266 (2016).
16. Pardee, K. et al. Portable, On-Demand Biomolecular Manufacturing. Cell 167, 248-259.e12 (2016).
17. Huang, A. et al. BioBits™ Explorer: A modular synthetic biology education kit. Sci. Adv. 4, eaat5105 (2018).
18. Stark, J. C. et al. BioBits™ Bright: A fluorescent synthetic biology education kit. Sci. Adv. 4, eaat5107 (2018).
19. Wen, K. Y. et al. A Cell-Free Biosensor for Detecting Quorum Sensing Molecules in *P. aeruginosa*-Infected Respiratory Samples. ACS Synth. Biol. 6, 2293-2301 (2017).
20. Takahashi, M. K. et al. A low-cost paper-based synthetic biology platform for analyzing gut microbiota and host biomarkers. Nat. Commun. 9, 3347 (2018).
21. Alligrant, T. M., Nettleton, E. G. & Crooks, R. M. Lab on a Chip Electrochemical detection of individual DNA. Lab Chip 349-354 (2013). Doi: 10.1039/c21c40993c
22. Fan, C., Plaxco, K. W. & Heeger, A. J. Electrochemical interrogation of conformational changes as a reagentless method for the sequence-specific detection of DNA. Proc. Natl. Acad. Sci. 100, 9134-9137 (2003).
23. Khan, H. U. et al. In situ, label-free DNA detection using organic transistor sensors. Adv. Mater. 22, 4452-4456 (2010).
24. Patolsky, F., Lichtenstein, A. & Willner, I. Detection of single-base DNA mutations by enzyme-amplified electronic transduction. Nat. Biotechnol. 19, 253-257 (2001).
25. Slinker, J. D., Muren, N. B., Gorodetsky, A. A. & Barton, J. K. Multiplexed DNA-modified electrodes. J. Am. Chem. Soc. 132, 2769-74 (2010).
26. Das, J. et al. An ultrasensitive universal detector based on neutralizer displacement. Nat. Chem. 4, 642-8 (2012).
27. Zuo, X., Xiao, Y. & Plaxco, K. W. High Specificity, Electrochemical Sandwich Assays Based on Single Aptamer Sequences and Suitable for the Direct Detection of Small-Molecule Targets in Blood and Other Complex Matrices. J. Am. Chem. Soc. 131, 6944-6945 (2009).
28. Kuang, Z., Kim, S. N., Crookes-goodson, W. J., Farmer, B. L. & Naik, R. R. Biomimetic Chemosensor: Designing Peptide Recognition Elements for Surface Functionalization of Carbon Nanotube Field Effect Transistors. ACS Nano 4, 452-458 (2010).
29. Liu, H., Xiang, Y., Lu, Y. & Crooks, R. M. Aptamer-Based Origami Paper Analytical Device for Electrochemical Detection of Adenosine. Angew. Chemie Int. Ed. 51, 6925-6928 (2012).
30. Das, J. & Kelley, S. O. Protein Detection Using Arrayed Microsensor Chips: Tuning Sensor Footprint to Achieve Ultrasensitive Readout of CA-125 in Serum and Whole Blood. Anal. Chem. 83, 1167-1172 (2011).
31. Tang, D., Yuan, R. & Chai, Y. Ultrasensitive Electrochemical Immunosensor for Clinical Immunoassay Using Thionine-Doped Magnetic Gold Nanospheres as Labels and Horseradish Peroxidase as Enhancer. Anal. Chem. 80, 1582-1588 (2008).
32. Sage, A. T., Besant, J. D., Lam, B., Sargent, E. H. & Kelley, S. O. Ultrasensitive electrochemical biomolecular detection using nanostructured microelectrodes. Acc. Chem. Res. 47, 2417-25 (2014).
33. Li, J. J., Geyer, R. & Tan, W. Using molecular beacons as a sensitive fluorescence assay for enzymatic cleavage of single-stranded DNA. Nucleic Acids Res. 28, E52 (2000).
34. Soleymani, L., Fang, Z., Sargent, E. H. & Kelley, S. O. Programming the detection limits of biosensors through controlled nanostructuring. Nat. Nanotechnol. 4, 844-848 (2009).
35. Green, A. A., Silver, P. A., Collins, J. J. & Yin, P. Toehold switches: de-novo-designed regulators of gene expression. Cell 159, 925-939 (2014).
36. Zhang, J. et al. Molecular detection of colistin resistance genes (mcr-1, mcr-2 and mcr-3) in nasal/oropharyngeal and anal/cloacal swabs from pigs and poultry. Sci. Rep. 8, 3705 (2018).
37. García, V. et al. Co-occurrence of mcr-1, mcr-4 and mcr-5 genes in multidrug-resistant ST10 Enterotoxigenic and Shiga toxin-producing *Escherichia coli* in Spain (2006-2017). Int. J. Antimicrob. Agents 52, 104-108 (2018).
38. Gootenberg, J. S. et al. Nucleic acid detection with CRISPR-Cas13a/C2c2. Science 356, 438-442 (2017).
39. 3Karig D K, Iyer S, Simpson M L, Doktycz M J. Expression optimization and synthetic gene networks in cell-free systems. Nucleic Acids Res. 40, 3763-3774 (2012).
40. J. N. Zadeh, C. D. Steenberg, J. S. Bois, B. R. Wolfe, M. B. Pierce, A. R. Khan, R. M. Dirks & N. A. Pierce, "NUPACK: Analysis and design of nucleic acid systems," Journal of computational chemistry 32, 170-173 (2011).
41. Davis J H, Rubin A J, Sauer R T. Design, construction and characterization of a set of insulated bacterial promoters. Nucleic Acids Res. 2011; 39 (3): 1131-41. 10.1093/nar/gkq810

The invention claimed is:

1. An RNA detection system comprising:

i) an RNA toehold switch-based sensor specific to an RNA target molecule, wherein the RNA toehold switch-based sensor comprises an mRNA sequence encoding a restriction enzyme, such that the restriction enzyme is translated upon binding of the RNA toehold switch-based sensor to the RNA target molecule;

ii) a reporterDNA/iDNA complex, wherein the reporterDNA is coupled to a redox active molecule, and wherein the restriction enzyme binds and cleaves to said reporterDNA/iDNA complex thereby releasing the reporterDNA; and iii) a captureDNA and an electrode, wherein the captureDNA is coupled to the electrode and wherein upon release of the reporterDNA, the reporterDNA binds to the captureDNA thereby producing an electrochemical signal detected by the electrode.

2. A method of detecting an RNA target molecule in a fluid sample, said method comprising:

a. providing a chip comprising the RNA detection system as defined in claim 1;

b. contacting said chip with the fluid sample; and c. detecting the electrochemical signal.

3. The system of claim 1, wherein said system is a multiplexed system for the detection of a plurality of RNA target molecules, said multiplexed system comprising a plurality of said RNA detection systems, and wherein each of said RNA detection systems comprises: i) a unique RNA toehold switch-based sensor specific to a unique RNA target molecule and comprises an mRNA sequence encoding a unique restriction enzyme; ii) a unique reporter DNA/iDNA complex; and iii) a unique captureDNA.

4. The system of claim 1, wherein said restriction enzyme comprises EcoRV, AciI, ClaI, BanII, BsaAI, BglII, BstEII, HincII, NcoI, or PstI.

5. The system of claim 1, wherein the redox active molecule comprises methylene blue.

6. The system of claim 1, wherein said captureDNA is coupled to the electrode via a terminal thiol group.

7. A method of detecting a plurality of RNA target molecules in a fluid sample, said method comprising:

a. providing a chip comprising the RNA detection system as defined in claim 3;

b. contacting said chip with the sample; and c. detecting the electrochemical signal.

* * * * *

SEQUENCE LISTING

<160> NUMBER OF SEQ ID NOS: 69

<210> SEQ ID NO 1
<211> LENGTH: 1850
<212> TYPE: DNA
<213> ORGANISM: Athrobacter citreus

<400> SEQUENCE: 1
gcgaattaat acgactcact ataggggaat tgtgagccga taacaattcc cctctagaaa 60
taattttgtt taactttaag aaggagatat acgatgggca gcagccatca tcatcatcat 120

```
cacagctctg gcatcgaagg gcgcagtggg ggaggagggt ccatgaatga gcacatcaag    180
ggctctaata gtcacggcaa ctcaaatgag ttggaattgg tttacgcctt tgacggtaag    240
aaggtcaaag atttgaatac caatcttaag aactttgtcc aattcattgc taatgacaac    300
aatattaaga ttaataatga tactaagctg ttcgcgaaat acgtaagtaa taataagctg    360
aaacaggact ttattgtttc attcaatgaa cgtgacttct atatcagttt gaagatgggg    420
agtggtaact ctgtgcatca ggagcccatt gaagatttca tcaaatactt gaacacaaac    480
tatgaagtaa cggagaagat ttgcaatgat cttcgctttt ttatctgggc agacggtaca    540
ttagacggca aggggaagtt cgagaatcgc ttcgatgctc gctattttaa gaagaactat    600
cccgagaagc gtcgcgaatt gttgcagttt ttcgagaaga acaaagtcga gctgattaag    660
cattttatgt tcgttggtaa acataattcg cgcgttgatt atctgtatca cggaactact    720
tccaacggag cctggatgtc aactaagcaa attattgatt ataatatcca aaaccagatc    780
gacacgaaca agggtaacag tccaacattg tctgttggac gtatgagcat ccaagcgtgg    840
aacgtcgcca aatccggatc tgaatcagcc gagaagaaac gtggtgaaat tcaagtgaaa    900
tacggaaagt taaaggaaga cttcaaagag gtacttaaac tgaatagtag caataaagga    960
actttatttg gagaccacga ggagtttgac atctccggaa cattgaacaa gaataaaaat   1020
cacttttact ggaagatgat cgcgcgcgac ttaaacttga atcaagaaga attaaataat   1080
ttatatgtgg tccgtgtaag ctcgaaagtt atgagcagtt tatctaaaaa gaaggtactt   1140
cccaaatctg acgcctacat tattcgcgca gacttgtcaa aatcattcct gcttagtaag   1200
gagtacaaac ttagcgaaga cgatcttgtt ggcatcattt acaagaaagt tggacgctcg   1260
ggaatttcgg taaaacgcgc agattccaaa aaatacacca ttgtaaaatt aacagttgcg   1320
agctttgaaa agtgctttga aatcgaacct gaaattaaga aaattatcgc cggtttactt   1380
ttatactcga aggaaaaaga catgtacaag aatttagaaa ttctgaacaa gatcggtatt   1440
agcgagttgg agcttatcaa ctacacaaac cgtttcattg tcgacaaggt aatttcatgc   1500
aatgacccga agaatgtaga tattattcgt tctacaatgc aggagcgtac acgtaccctg   1560
attgagaaga atcttgagat caaaaaagca ttgttcatgg gtgagggttg gtacgaggag   1620
ccatactgca tcaactatat ttttaaggat ggaaaattat cgaacgacgt gttttccgag   1680
tacatcatta ctacgggcag tggtcgttca aaggggaatt atacgattgc cttgaaacca   1740
aagagtggag gaggaggcag tgaaaactta tacttccaga gcagctctgg cgactacaaa   1800
gatgatgatg ataaataact agcataaccc ctctctaaac ggaggggttt              1850
```

```
<210> SEQ ID NO 2
<211> LENGTH: 1103
<212> TYPE: DNA
<213> ORGANISM: Thalassobius gelatinovorus (Ruegeria gelatinovora)

<400> SEQUENCE: 2

gcgaattaat acgactcact ataggggaat tgtgagcgga taacaattcc cctctagaaa     60
taattttgtt taactttaag aaggagatat acgatgggca gcagccatca tcatcatcat    120
cacagcagcg gcatcgaagg gcgcagtggg ggcggagggt ccatgcgcct ggatctggat    180
tttggccgcg gcctggtggc gcatgtgatg ctggataacg tgagcgaaga acagtatcag    240
cagattagcg attattttgt gccgctggtg aacaaaccga aactgaaaag ccgcgatgcg    300
attggccagg cgtttgtgat ggcgaccgaa gtgtgcccgg atgcgaaccc gagcgatctg    360
tggcatcatg tgctgtatcg catttatatt cgcgaaaaaa ttggcaccga tccgagccag    420
```

agctgggtgc gcaccagcgg cgaagcgttt gaagtggcgc tggtggaacg ctataacccg 480
gtgctggcgc gccacggcat tcgcctgacc gcgctgttta aaggccagaa aggcctggcg 540
ctgacccgca tgggcgtggc ggatcgcgtg ggcagccgca aagtggatgt gatgattgaa 600
aaacagggcg gaggccgcag cccggatgcg gaaggctttg gcgtggtggg cggcattcat 660
gcgaaagtga gcctggcgga acgcgtgagc gatgatattc cggcgagccg cattatgatg 720
ggcgaaggcc tgctgagcgt gctgagcacc ctggatgtga aaagctttcc gccgccgcat 780
ggcgatctgg tgaaccgcgg cgaactgggc accccggatc gcccgagcga taaacgcaac 840
tatattgaag gccacggaga ttttagcgcg tgctttagct ataacctgag gaccagcccg 900
agcaacgcga ccaccccgtc cggccgccat atttatgtga gcggctttag cggccaggat 960
gatgaattta ccgattatct ggtggcgcag ctggcgagtg gaggaggagg cagtgaaaac 1020
ttatacttcc agagcagcag cggcgactac aaagatgatg atgataaata actagcataa 1080
cccctctcta aacggagggg ttt 1103

<210> SEQ ID NO 3
<211> LENGTH: 1493
<212> TYPE: DNA
<213> ORGANISM: Cellulosimicrobium cellulans

<400> SEQUENCE: 3
gcgaattaat acgactcact ataggggaat tgtgagcgga taacaattcc cctctagaaa 60
taattttgtt taactttaag aaggagatat acgatgggca gcagccatca tcatcatcat 120
cacagcagcg gcatcgaagg gcgcagtggg ggcggagggt ccatgggcag cattgtggtg 180
gatcagattg gcccggatgg cgaactggtg ccggatgtgg ataccaccct gagcgaaaaa 240
gaaaaaaacg atctgctgct gagcgcgctg ccgggcgcga ccaccagcac ctatggcggc 300
gcgcgcgtgg tgcgctttca tgatcagatt attctgaaag cgcaggtgac acatctgggc 360
catccgtggc cggcgtataa aaaacgcatt cagattccga aatcatggct ggaagtggaa 420
cgccgcgcga cccgcgatgg cctggtgacg cgctttgtgg gcatttatcg ctatcgcgcc 480
gttaccgtgt ttgtggattt tgatccgcgc acctatattc agcgcgcggc gaacaacagc 540
gcggcgcatg tgagcaccaa cgatctgcat caggcgcaga ccctgggcct gtttgaacgc 600
gtggatcgca acggcaactg cctgaccagc gtgcgcgcgg aactgctggc ggattatctg 660
gtgggcgtgg cggataccac ccatccgagc gtggatgtgt ttcgccgctt taaccaggat 720
ttttttaccg gccgctggct gcgcgcgctg gatgcggtgc aggaaatgca tgcggcggcg 780
tggccggatc gctttcagaa cgaatgggcg ggcttttatc tggaatatcg ctttgatcgc 840
tttgtgcgcg cggaaggcct ggcggatatt gtgcagtttc agaaaaaaaa acagcgcggc 900
ggctatgatt atgatctggt gtttcatgat ggcccgcgcg tggattttta tggcgatctg 960
aaagcgagca acattgcgaa acaggaagcg attggcaacg atcgcgatga tctggtgcgc 1020
tgcctggaag aatttggccg cttttggtat gtgatttatg aacatgatac cgtgcatggc 1080
aaagcgaacg gcgatgtggc gaccattgaa tggaacgaat ggcgccgcag cgtgggccat 1140
gtgcagggca aagaatatag cccgctgagt tacagcggcc gctttaaaga aagcgtgcgc 1200
tttgcgcgca tgcaggtgct ggaagtgaac gaagcgaacg cgagcctggt gctgggcgat 1260
catcatcagg gccgccagcc gagcggcgcg agccgcgaac cgaaagtgaa aattctgaaa 1320
aaacatattg ataactttct gatttttagc agcgcgctgc cggaagtgcc gagcggcctg 1380

```
cgcgtgagtg gaggaggagg cagtgaaaac ttatacttcc agagcagcag cggcgactac   1440

aaagatgatg atgataaata actagcataa cccctctcta aacggagggg ttt          1493


<210> SEQ ID NO 4
<211> LENGTH: 1334
<212> TYPE: DNA
<213> ORGANISM: Acetobacter pasteurianus

<400> SEQUENCE: 4

gcgaattaat acgactcact ataggggaat tgtgagcgga taacaattcc cctctagaaa     60

taattttgtt taactttaag aaggagatat acgatgggca gcagccatca tcatcatcat    120

cacagcagcg gcatcgaagg gcgcagtggg ggcggagggt ccatggctcg taatgtgtta    180

gtcgaacgcg ccgttgacgc cgctctggag cgtttagatg cttttatcga aggggagaag    240

cttgctaaat tacccgatgc ggcgacgcgt gctctgttag acgaccaact ggggcatggc    300

tctaacagtg tccgtttagc ctcgttgttc ttcgtgtttt atgcctctgt cgatttggcg    360

tgggattgca actccatccc gactggcatc cgcggcacgt atggggacaa acgtttagcc    420

acacaattag gattacgttc catcacgctg cataatgcca ttacggcatt cggtgagaac    480

ctggggtgga aaggcaacgt cactaatagt cgccttcaaa acgatgtacg tttcgacggc    540

ttcggccgca ccttgacggg gctgaacgtg gaacaacgca cgttatgtgc tgattacatg    600

gcggcccgct tcgcagaatc acgcaaggtc atcgctccat taccaccagt ggctgatgac    660

gtcttgactt atgcccgtgc tcgcaagtta ttctattcgc tgattgccct tccgagtgaa    720

ggcaatgtgc aacagttttt aatcgctgcc ctgctttttg tacatcgtca acgttacggg    780

tatgatattc gtactcacca tgtccatgcc agcgaccgct tcgacaccac ggcgggtgac    840

attgaagaat tgctgaacgg cgatttggtc cgcgcgtatg aggtgacagt gcgccccgat    900

tggaagaacc gtatgggtga ctttcgcaaa aaaatggacg gggcatcctt gcgtaaatat    960

actattatcg catccaacgt taattccgac gacgacctgg ctgagccagc ggacatgatc   1020

cgtttcctga cgccttacgg tcgtgatatt gcgattgtgg acatccacga cttcatcaat   1080

gtgttcgcaa tggaactgat cgtagacgag ctttgtcgcg cagtaactca aacgtataac   1140

tacttgacga caccatctct ttgtggccgt gcagacatta ttgacaagtt caatgcgacg   1200

gtagaggggt ggctggatga ggttactagt ggaggaggag gcagtgaaaa cttatacttc   1260

cagagcagca gcggcgacta caaagatgat gatgataaat aactagcata acccctctct   1320

aaacggaggg gttt                                                     1334


<210> SEQ ID NO 5
<211> LENGTH: 920
<212> TYPE: DNA
<213> ORGANISM: Bacillus cereus

<400> SEQUENCE: 5

gcgaattaat acgactcact ataggggaat tgtgagcgga taacaattcc cctctagaaa     60

taattttgtt taactttaag aaggagatat accatgggca gcagcgatta taaagatgat    120

gatgataaag gacatcatca tcatcatcac agcagcggcg agaacctgta cttccaatcc    180

tctggaggtg ggggttctat gaagatagag aaggagttta tcactgagac ggccaaaaat    240

cttttgctga cggactcgct tattgaacag gcatataaag aggtcaaaac gagcatctgt    300

agtccagtat ggccaatgga gtcaaaaatc ttcactgtta acaatacaaa aaagaattgt    360

aatggggtgg tgcctatcaa ggaactttgt tacacgacgt tggaggagac gtataattgg    420
```

```
tatcgtgaga agcctcttaa tgtgttaaaa gttgaaaaga aaaaaggagg ccctatagat    480

gtttataagg aattcagcgc tggtttaagt gaaaaaaagg aattggataa tttggaagga    540

ctgaatcaag ttgacaacat acggcgggta ggaatggaat ttgagacggg caatatatct    600

tcggcacaca gatctatgaa caagttactg cttggactga aaagagagga aatcgacctg    660

gcaattatac ttatgccaat aaagaagctg gcttactact tgacggatcg cgttaccaac    720

tttgaagaat tagaaccgta ttttgaattg acagaggggc aaccgttcat gtttatagga    780

tttgacgcag aagcctacaa cgtgaatgta cctgtgatcc ccaaagggag cgatggtatg    840

tctgaccggt cgataaagaa gtggaaggat aagattgaag atctttaact agcataaccc    900

ctctctaaac ggaggggttt                                                920
```

<210> SEQ ID NO 6
<211> LENGTH: 1361
<212> TYPE: DNA
<213> ORGANISM: Aneurinibacillus aneurinilyticus

<400> SEQUENCE: 6

```
gcgaattaat acgactcact ataggggaat tgtgagccga taacaattcc cctctagaaa     60

taattttgtt taactttaag aaggagatat acgatgggca gcagccatca tcatcatcat    120

cacagctctg gcatcgaagg gcgcagtggg ggaggagggt ccatggaaca agttaccatt    180

aaccacgaaa aagccaagct agtattagag caggctttta aaactgctaa ttctggggat    240

tatactccta gctctaaatt tgctgatgct atccatactg ttttatttaa tacacactta    300

acttttaaat atattttggt taacgcatta ttagctaaag cttcttttcc acaaataaat    360

cctatatgtt tacagaaaaa atctacactt tctggtgctt atgatgctag gtccctttgt    420

cataaagtat tagttccttt tgaacggaac aacctaaatg gagcattagg aaattcaaat    480

gagccttttt taaataagcc tgcacgtttt actgaattaa gcccaaaaaa tgcagtacgc    540

aaaggtagag atagtatgtt actaaatctt ctttgtgatt ttttacctca gattaattca    600

caaaatgaag cttttcattc tttaacagac gcattatttt atgcattaca attggctaaa    660

aataaacaac aaaaatttaa ttttacatca ataaaaacac ctacttatac cgacatagaa    720

atttttatta aagaactctt ggaagaatct tatggtggag aatgtctagc tttagccata    780

ggcactttat taaaacttaa atccgaaacg ataattggtg aaaatagagt cgaagtacat    840

gttgttaacc agtcaggtgc ttcttctaaa gaagtaaacg atattgatgt ataccatgaa    900

gatgaaattt tatatacaat tgaagccaaa gataaacatt actcacaaca agatgtagaa    960

catgcagtga gaaagacagc cgaagctgga tgcgatagac taacttttat aacaggacca   1020

cgtgctaaat ttgatggttc tcacaccacg ttagttttaa gcgcctccaa attaggagtt   1080

tatcttacat ttacaagtta cgaagctttc acaaaaaaca tcttatcttt aattttaccg   1140

aaaacagcta atgatttctt caaactattg atgcatacat gcgatgaagc aagagtaaaa   1200

gaagaaacgc tcaatcacgt aatcaaaaca gcacgtaacc atcagttaat cgaaagtgga   1260

ggaggaggca gtgaaaactt atacttccag agcagctctg gcgactacaa agatgatgat   1320

gataaataac tagcataacc cctctctaaa cggaggggtt t                       1361
```

<210> SEQ ID NO 7
<211> LENGTH: 902
<212> TYPE: DNA
<213> ORGANISM: Bacillus atrophaeus

<400> SEQUENCE: 7
gcgaattaat acgactcact ataggggaat tgtgagcgga taacaattcc cctctagaaa 60
taattttgtt taactttaag aaggagatat accatgggca gcagcgatta taaagatgat 120
gatgataaag gacatcatca tcatcatcac agcagcggcg agaacctgta cttccaatcc 180
tctggaggtg gggttctat gaagatcgat ataaccgact ataaccatgc tgacgaaatt 240
ttaaatcccc agttatggaa ggagatcgag gaaactctgc tgaaaatgcc tttacatgtc 300
aaggcctcag accaagcgag caaagttggt tcattgattt tcgacccagt aggtacaaac 360
caatatatta aggatgaatt ggtgccgaaa cactggaaga acaacatacc gattccgaag 420
cggttcgatt ttctgggtac agacattgac tttggtaaaa gagacactct ggtcgaggtc 480
caattctcga actatccctt tcttttgaac aacacggtac ggtcggaact tttccacaag 540
tcgaatatgg acattgacga agagggaatg aaggtggcaa tcataataac taagggtcat 600
atgttcccag ccagcaattc ttcattgtac tacgaacaag ctcaaaacca attaaattca 660
cttgccgagt acaacgtttt cgatgtcccg atcagacttg tgggtctgat cgaggacttt 720
gagacggaca tagatatagt ctctacgaca tatgccgata agcggtattc cagaactata 780
acaaagcggg acacagttaa gggaaaggtc atagacacga atacgccaaa cacccggcgt 840
cggaaacggg gcactattgt cacgtactaa ctagcataac ccctctctaa acggaggggt 900
tt 902

<210> SEQ ID NO 8
<211> LENGTH: 3296
<212> TYPE: DNA
<213> ORGANISM: Bacillus pumilus

<400> SEQUENCE: 8
gcgaattaat acgactcact ataggggaat tgtgagccga taacaattcc cctctagaaa 60
taattttgtt taactttaag aaggagatat acgatgggca gcagccatca tcatcatcat 120
cacagctctg gcatcgaagg gcgcagtggg ggaggagggt ccatgcatat aagtgagtta 180
gtagataaat acaaagcgca tagaagtact tttttaaaac caacttataa tgaaactcaa 240
ctaaggaatg attttataga cccacttcta aaatctttag gatgggatgt tgataatacc 300
aaaggaaaaa cacatattct aagagatgtc attcaagaag aatacataga aataaaagat 360
gaggagacaa agaaaaatcc agattataca cttcgtataa acggtacgag aaagctgttt 420
gtagaggtta agaaaccgtc ttttaatatt ttgaaatcag ctaaagcagc cttccaaaca 480
agaagatatg gttggagtgc taaccttggt atttcagtac ttacaaattt cgagcatcta 540
gttatttatg attgtagata tacgcctgac aaatccgaca atgaacatat tgctagatat 600
aaagttttct cttacgagga atatgaagaa gcatttgatg aaataaagga tataatttca 660
tatgagtcag ccaactcagg tgctctggac gaaatgtttg atgtaaatac aagagttggt 720
gaaacgtttg acgagtattt tttacagcaa attgagaatt ggcgcgaaaa gctagctaaa 780
actgcaatta aaaataacac cgaattaggt gaagaggacg tcaattttat tgtccaaaga 840
ctattaaaca gaattatttt tcttagagtt tgtgaagata gaaccattga aaaatatgaa 900
acaattaaaa gtataaaaaa ctatgaggaa ttaaaagatc tgtttcaaaa gtctgatagg 960
aaatttaatt caggtctctt tgacttcata gatgatacgc tcttgcttga ggttgaaatt 1020
gattcgaatg tattgataga aatttttagt gatttatatt tcccacaaag cccatatgat 1080
ttttctgttg tcgatccaac aatattaagc cagatatatg aacgttttct aggtcaagaa 1140

```
ataattatag agtcaggtgg tacatttcac attacggagt caccagaagt tgcagcgtcc   1200
aatggtgttg ttccaactcc aaaaattatc gtcgaacaga tagtgaaaga cactttaacg   1260
ccccttacgg aaggcaaaaa atttaatgag ctatgtaact taaaaatagc agatatatgt   1320
tgtggatcag gaactttcct aatttcaagt tatgactttc tagtagagaa agtaatggaa   1380
aagataatag aagagaacat tgatgattca gatttagtat atgaaactga agaagggcta   1440
attttgacac ttaaagcaaa aagaaatatc ttggagaata atttgtttgg tgttgatgtt   1500
aatccatacg ctgttgaagt agctgagttc agtttattat taaagctatt agaaggtgag   1560
aatgaggcat cggttaataa tttcattcac gagcatgagg ataaaatatt accggattta   1620
acatctatta ttaaatgtgg aaacagctta gtagataata agttttttga attcatgcca   1680
gaatcgttag aggacgatga aatcttattt aaggctaatc catttgaatg ggaagaggag   1740
tttccagata ttatggcaaa tggtggcttt gatgctatta taggaaatcc accttatgtt   1800
cgaatacaga acatgaaaaa atatagtcct gaggaaattg aatattatca atcaaaagac   1860
tctgaatata ctgttgcaaa aaaagaaaca gttgacaagt attttttatt tattgagaga   1920
gcattaatat tactcaatcc tactgggctg ttgggttata taataccaca taaattcttt   1980
attacaaaag gtggtaagga actaagaaag ttcatagctg aaaaacatca aatatcaaaa   2040
attataaatt ttggtgttac acaggtcttt ccaggaagag cgacatatac ggctatttta   2100
attatccaag caaataaaat ggcacagttc aagtataaga aagtaagtaa tatatcagca   2160
gaaaccctag attctgaaga aaatacgtgt gtttatagct cagaaaagta taattctgac   2220
ccttggatat ttttatctcc tgaaacagaa gctgttttta ctaaatttac agaagctcaa   2280
tttgagaaac ttggagaaat cactgatata agtgtaggac tacaaacaag cgctgataaa   2340
atatatattt ttattcctga aaatgaaact tcagatacat atatatttaa ttataaaggg   2400
aaaagatatg aaatagaaaa atctatatgt tgcccagcta tctatgactt atcttttggt   2460
tcttttgaaa gcattcaggg aaatgcacaa atgatattcc cttatgaaat cagagatgaa   2520
gaagcatatc tactagagga agaaacgctt gaaaatgatt atcctcttgc ttggaattat   2580
ttgaatgagt ttaaagaagc tcttgaaaaa agaagcttac aaggccgtaa tccgaaatgg   2640
tatcaatatg gtcggtccca aagtttatca aaatttcatg ataaagaaaa actgatatgg   2700
accgtacttg ctacgaaacc cccgtatgta cttgatagga ataacctgtt atttactggt   2760
ggtggaaacg gaccgtatta tggtttaatt aaccaatcta tttactcttt gcattatttt   2820
ttaggtattc tttcacatcc tgtaatagaa agtatggtaa aagcaagggc cagtgaattt   2880
aggggatcat attattctca tggaaaacaa tttattgaga aaatcccaat tagaaagatt   2940
gattttgatg atcaagatga ggtagacaaa tataatacgg tggtcacaac agtagaaaaa   3000
ttaattataa ctaccgatag aattaaaagt gagagcaatg gaccccggag gagaatgtta   3060
agaagaaggt tagatgcttt gtctaatcaa cttatccagg ttattaatga actttataat   3120
atcagtgacg aagaatatac gacagttttg aatgatgaaa tgttgacagc agcgttagga   3180
gaagaaaaaa gtggaggagg aggcagtgaa aacttatact tccagagcag ctctggcgac   3240
tacaaagatg atgatgataa ataactagca taacccctct ctaaacggag ggttt        3296
```

<210> SEQ ID NO 9
<211> LENGTH: 1049
<212> TYPE: DNA
<213> ORGANISM: Geobacillus stearothermophilus

<400> SEQUENCE: 9

```
gcgaattaat acgactcact ataggggaat tgtgagccga taacaattcc cctctagaaa     60
taattttgtt taactttaag aaggagatat acgatgggca gcagccatca tcatcatcat    120
cacagctctg gcatcgaagg gcgcagtggg ggaggagggt ccatgtacaa ttatttatta    180
aacgaaaatg cagatataat ttatgatgga aaggttatac tcacaaaaga acaagttgtt    240
gaagcaatta ttataacaaa tacaaactta aagaaactta atgacattac gaaagagtct    300
ggtgtcgaag tgtttgaagc attaggaatg agaaacctaa gtggttttat tggtgagttt    360
ttcgtaagca gtctcgaaca agtatcaaat aagaacttag ttaaaaatcc acatcaagat    420
ggatacccag atttgttgct cgtagattct cctaaagctg cctcatactt taattcaata    480
gtcgaaatag ttgatggaaa attatatcca aaagaaaaaa gtctgtttag cccatttaaa    540
tatggtggat tagaggtaaa agccacttgt ggttctacac cttcagcaaa agttatgcct    600
aagccattga ttggcgagca gagaattcac atcttaactg gattagattg gaaggcccat    660
catagaggta ctaacaatct aataggaata tattgggatt ttttagatga gttaccaacc    720
atttgcgctg tattttatag aaacgaccta accgaagatg attggggaaa aattgttcgc    780
cctaaagaag gtgggggaag aaccacaagt gtatccatta tgaactcaaa gggtgtcaaa    840
aaaatgtgca agaactggat tgctattatt gataacgaag attatataaa cgcattttct    900
aataaaaaat ggataggata taatgtaaaa aactcatcaa atagtggagg aggaggcagt    960
gaaaacttat acttccagag cagctctggc gactacaaag atgatgatga taaataacta   1020
gcataacccc tctctaaacg gaggggttt                                     1049
```

<210> SEQ ID NO 10
<211> LENGTH: 1379
<212> TYPE: DNA
<213> ORGANISM: Geobacillus stearothermophilus

<400> SEQUENCE: 10

```
gcgaattaat acgactcact ataggggaat tgtgagccga taacaattcc cctctagaaa     60
taattttgtt taactttaag aaggagatat acgatgggca gcagccatca tcatcatcat    120
cacagctctg gcatcgaagg gcgcagtggg ggaggagggt ccatgtcaga aagaaaaccg    180
ggattgtttg gtttaaagaa atcaaacaga gattttacta aaaaagaaaa ctggggtaaa    240
aatcaattta atagttcttt tcctgctgct ctggcttgct atatggagtc caaaggaatt    300
gaacctgtat atctgtattt agataaagtt caagaaggat taataggaga ttctctaaaa    360
gttcaacacg ggaaaataaa cgtaagagac ctattcggac ttccaccaca tgtaagcatg    420
gaggatgttt attttgaatt tgagggatta tttgctcctc attctcactt tgaacgtgag    480
gggtcagaac caccacgaaa tgaccttgta atacgaaatg aagaaggaac ggaatattat    540
agaggccttg aagttaaatt aactacaatt ccagatcata ctacacatga attagatgaa    600
gaacattacg gttgtgagtt agttattcgt tctgttacta tcgttcattt agcgattacc    660
attgctgaaa tatatgaaaa taatagagaa gaactatata atatattaaa tcctattaca    720
caaaatataa ataattggct tgatgaacct actttaataa acttattacc taacatgata    780
aatgcaatta atactatatt aataaataat ctcgataaac aagaaccact aattctcaac    840
cctatttgga agacaaatgg taagtcctct gcattatctg attactgttt agatattttt    900
gtatggagta attttgcttt aactcgttta tttattgatt ctattaaagt taatagaaca    960
tttattgata gatattcaag atcattagtt tggttaatca gactactaga tgaattcgca   1020
```

```
aaacgtggta aaatggatta tagaaaaatt tacggcatgc cttttaattc tcaaactgat   1080

aaggcattcg ctgtttcagg taaaaaaact catccataca tggcatgtgc tgaattaact   1140

aaaccaagaa taagaagaga ggaaatcgga aatatcattt taaatgatgg ccaattactt   1200

ttaagccctg agcgacgttt tgatgcagct attgtgtatt caccagatat tttcgaaaat   1260

cagcaagaga ggagtggagg aggaggcagt gaaaacttat acttccagag cagctctggc   1320

gactacaaag atgatgatga taaataacta gcataacccc tctctaaacg gaggggttt    1379
```

<210> SEQ ID NO 11
<211> LENGTH: 1097
<212> TYPE: DNA
<213> ORGANISM: Geobacillus stearothermophilus

<400> SEQUENCE: 11

```
gcgaattaat acgactcact ataggggaat tgtgagcgga taacaattcc cctctagaaa     60

taattttgtt taactttaag aaggagatat accatgggca gcagcgatta taaagatgat    120

gatgataaag gacatcatca tcatcatcac agcagcggcg agaacctgta cttccaatcc    180

tctggaggtg gggttctat gataaagaac ttccgggact accagagagt agctgccaaa    240

tatataacgt tcatcgaatc agagttctac cctgactatt tggataatgc ccgtttttta    300

tatggggaag tgcttaataa attctacgaa ctggtgaact cgtcctccag ctcaatagaa    360

ttgcttgaga atatttccaa gacgaaagat cctgtcagaa cccagttatt acgcattttc    420

agaaagtacg tgtcaccgga taccagcgtc gagatgttaa agcggaagca gcgtattccc    480

gatatcatca aggagttcgg cacaagattt cgcgacatta aaatcgttag acagaagatt    540

gccacaagaa accatccaga tgaaacaatc atggcattac tgtatgaata taaagacaga    600

ggaaagaaag ggtatgaatt gacggatgcc ttcttcacat ggttcgaaca aaagtttcct    660

aattatgaga ttataggtcc tcgtggcgca ggtaaagaca tattacttaa cgaagtgctg    720

ccaggatttc cgtcgaagat acctgcggac ttcctgattt atagacgctc ggataagaca    780

cccatagtcg taggttttgc tcggtatgat tctgatcgcg ggggggcgca ggaggatgat    840

cgcaccggcg gcaatagaga taagattacg gagatcaaaa aatatgctgc tgaacacaac    900

ataccgttga aaatcttatt cttaaatgat ggccccggtt tgctgcttgg ctctatgtgg    960

aatgattact cagccttgga agattatggg gaggggtgcg tcatggtttg tacccttaaa   1020

atgcttgagg agcggttcac tatcgactgg cttgagaacc tttaactagc ataacccctc   1080

tctaaacgga ggggttt                                                 1097
```

<210> SEQ ID NO 12
<211> LENGTH: 1346
<212> TYPE: DNA
<213> ORGANISM: Caryophanon latum

<400> SEQUENCE: 12

```
gcgaattaat acgactcact ataggggaat tgtgagcgga taacaattcc cctctagaaa     60

taattttgtt taactttaag aaggagatat acgatgggca gcagccatca tcatcatcat    120

cacagcagcg gcatcgaagg gcgcagtggg ggcggagggt ccatgacgta tttaattttg    180

cgtcgtcagc agcgtatgaa aaattcagca cagatgatta aagacaacat catgaaggag    240

caattaacga tttatcatga gatcgaagtc ggagatccag aattttggta ttccacggag    300

cagatggaag aattactgaa tgaagcatta caaggcactg atttgaatgg tatggcgctt    360
```

```
cgcacgcgct ctaaattcgt caaagtcaaa atctgtgagg cgttcggtta tcaggtgccg    420

aaatctttta aaaagactca acctcgcttt ttatctcaaa agttcgacgt ttataaccaa    480

aagagtaaca atttacagat ttggaatgaa gaaatttcac cctctcgtcg ctatgtatta    540

atcaaaatca gttttgatga cattattact caagtaaagg ttgtcacggg cgatgtcctt    600

gcgacgttgg attctacggg tacacttaca caaaaaatatc aagctaaata cgctggagtg    660

catgaacgca aggccactct gctttcagaa tgtgacacgg attttattca atccatcacc    720

caaagctata atagcttcga tgaatttacg gcacctgaca ctaatcccaa agaggacgaa    780

ctgatgggta tagatgaaat ctttgataag ttgaaggact taattggcac caaaatcccc    840

tatatcggtg cgacgcagga acgtaatcgt gggggccatc ttcataagat gatttgcgat    900

gcactggggt acaataattt taaagagaat ggacagttcc ccgacattaa acatcagctg    960

ttggaagtaa agttgcaaac gtcggaaact attgaccttg gactgtttac acctaacagt   1020

tacgagctgc ttgatatacc tcaacttaac aatgaatcca ttagtatgct ggatgtgcgc   1080

tatgcgattt tctatggaga tgtgatcgag gatactatta ctattacaca tttctacctt   1140

gttacaggtg aagacttctt cacgtacttc aaaccatttg ggggcaaggg aattaataaa   1200

aagattcaaa ttccccttaa cgaagagttc tggaacttga gtggaggagg aggcagtgaa   1260

aacttatact tccagagcag cagcggcgac tacaaagatg atgatgataa ataactagca   1320

taacccctct ctaaacggag ggttt                                         1346
```

<210> SEQ ID NO 13
<211> LENGTH: 1163
<212> TYPE: DNA
<213> ORGANISM: Paramecium bursaria

<400> SEQUENCE: 13

```
gcgaattaat acgactcact ataggggaat tgtgagccga taacaattcc cctctagaaa     60

taattttgtt taactttaag aaggagatat acgatgggca gcagccatca tcatcatcat    120

cacagctctg gcatcgaagg gcgcagtggg ggaggagggt ccatgttgac agaaacgtta    180

gttcgtcgtt tcgtgaaaaa ggcgattaaa aatgtcattg acatggataa gaaaagaatg    240

aaagcagaga ttaaactcgc aaaagctcaa gcaaaggaac aagaaaaaga ggcaaagcgt    300

atcattcgag agaacaatcg catattcaaa aaagctttga agatgaatct gccagataat    360

gaacctattt ccgatgatga catcgtttat gatgattcac atatagaaaa aggtgttcag    420

agccaacatc atgggtttgt attcgaaaac gagttgcgcc ataaggtgtt cttgattccg    480

actcgatcta acgatgtgaa tacacacgac atatcaaaga accagaaccg atttgatgcc    540

atcgaaaaca tttctatcaa gaccacaggc aaaaaagaca tctgttgtgg agacatcatt    600

cgtttttatg attatgattt ttcggatgcc aataccatga tagtaggaca atatactcaa    660

actacaaccc ataaaaaaat agacagaatt atagaaataa aatacgataa aaaactacac    720

gaagttctat tcggaaccat cacaagggac gaactcatcg cttatgttga tatggtaaag    780

gcattgccac gtggaaggat ctctaagagc aaacgcgatg aaattctgtc tatgaagaag    840

gaacttgaaa agacacatgg tatgtatata cagatctcgc ctaagattga tagtggaaat    900

caaagacgcg ttcaatgtcg cataagaaat gtcgatgatc tagtagaaaa gaaccccgaa    960

aatctgttaa gtatttctac tacaggtgtc gtgcgtggca ttgctataaa taccatcata   1020

gcttcttaca ggaggaatcg cactgccagg ttgagaagtg gaggaggagg cagtgaaaac   1080

ttatacttcc agagcagctc tggcgactac aaagatgatg atgataaata actagcataa   1140
```

cccctctcta aacggagggg ttt 1163

<210> SEQ ID NO 14
<211> LENGTH: 989
<212> TYPE: DNA
<213> ORGANISM: Desulfovibrio desulfuricans

<400> SEQUENCE: 14
gcgaattaat acgactcact ataggggaat tgtgagcgga taacaattcc cctctagaaa 60
taattttgtt taactttaag aaggagatat acgatgggca gcagccatca tcatcatcat 120
cacagcagcg gcatcgaagg gcgcagtggg ggcggagggt ccatgaaagc cgcgacagac 180
caggagctgc gcaaattgat tgtgttgtat aataacgtga tggaggttat ggaacatgac 240
gccgcgaagt cgatgcgtga cgacaaccgt gcgtatggag ggtttgtccg cgccgcgaaa 300
ggcaagattc aggaattaat tacagagcgc ctggtgcgta cggtttggga tgtagaaatg 360
ggggaaaatc ccgaacgtct ttcgatcaat agcaagaaaa tcaaaatccc catcctgcgt 420
tcctacgtgg atagtattaa cgatgaaaac ttgaaaaaat acatctcttc taacatctta 480
aagtactcgt atggcttaag cgtagacaag catgtcttca ttgataataa attcgttctg 540
ggaattgagt gcaaagcata caccgaaaat gcgatgttga agcgtatttt ggtggacttt 600
tacttattga agaccaagtt ccctaaattg aactgtttcc ttttccagct ggagtctcaa 660
cttgggggag attatagtga gtgtaataaa tttcctatcg gctcgtatcc cacacgcacg 720
atcatgtctt actttaaaaa tgtagatttg aacatcgtta cgttacttga gggtgaacgc 780
aaagtcgacc gccctatcaa taagccacag ttttttaagc ctttgaaggt ggaacacctg 840
gaagtagcta ttggctacct gcaagagtcg ttgtcagaaa tcagtggagg aggaggcagt 900
gaaaacttat acttccagag cagcagcggc gactacaaag atgatgatga taaataacta 960
gcataacccc tctctaaacg gaggggttt 989

<210> SEQ ID NO 15
<211> LENGTH: 1175
<212> TYPE: DNA
<213> ORGANISM: Escherichia coli

<400> SEQUENCE: 15
gcgaattaat acgactcact ataggggaat tgtgagcgga taacaattcc cctctagaaa 60
taattttgtt taactttaag aaggagatat accatgggca gcagcgatta taaagatgat 120
gatgataaag gacatcatca tcatcatcac agcagcggcg agaacctgta cttccaatcc 180
tctggaggtg gggttcttt gattagtaca agttatgccg ctaacagtaa aagttacaaa 240
ggttatcaac ctactttatt tgaaagtgaa aactcacact ttgatataaa caaaaccgtt 300
caaaatggca aaatatttac attaagccgt gacgtaaacg gtgataaaaa aattgatatt 360
aatgatttgg actgggatta tttacaaggg gatggtgatt ttcgtagtga tgaagttaaa 420
gcattacgca acgaagctga cattattata actaatccac ctttttcgtt atttcgtgaa 480
tttttagctt ggattgttga agctaataag aaattcgtca ttatcggtaa tatgaacgca 540
atcacctaca aagaagtttt tcctttaatt aagcataata aaatgtggtt aggtccaact 600
attagtagtg gcgatagaga gttccaagta ccagatgaat atccaattaa tgctgtcgga 660
tggcggattg gtgaagatgg ccgaaaatat ttaagaatta aaggtgtgcg ttggtttact 720
aattttgatc atggtcgtcg ccatgaacca ttacaactga tgactatatt ggataaccta 780
aagtttaata agaaaatgca agccaagacc aattatgaca gttatgacaa ttacgatgca 840
atagaagtgc cttttactag tgcaattcct agtgattatg acggtgtaat gggtgtgccc 900
attagctttt tggataaata taatcctgac cagtttgaga tagttgggat gtgtgaaaac 960
gcagatttat atgatttaaa aacaaaaaat tataatacag tggaatgcaa gcaagcatat 1020
tttgacaaat ttggaaagaa gggaacttat gacttaaatg cgagtggagt tgtttacaga 1080
gatgggcttt tggaaaaagt ttatcaacga gtgctcataa aacataggaa tgtagctata 1140
tgactagcat aacccctctc taaacggagg ggttt 1175

<210> SEQ ID NO 16
<211> LENGTH: 968
<212> TYPE: DNA
<213> ORGANISM: Escherichia coli

<400> SEQUENCE: 16
gcgaattaat acgactcact ataggggaat tgtgagcgga taacaattcc cctctagaaa 60
taattttgtt taactttaag aaggagatat accatgggca gcagcgatta taaagatgat 120
gatgataaag gacatcatca tcatcatcac agcagcggcg agaacctgta cttccaatcc 180
tctggaggtg gggttctat gagtcttcgt tctgatttaa ttaatgcact atatgatgaa 240
aatcaaaaat atgatgtatg cggaataata tctgcagaag gaaaaatata cccattggga 300
agtgacacaa aagttctaag cacaatattt gagttattct caagaccaat aataaataaa 360
atagcagaaa aacatgggta tattgtagaa gaacctaaac aacaaaatca ttatcctgac 420
tttactcttt acaaaccaag cgaaccaaat aaaaaaattg caatagatat aaaaacaaca 480
tatacaaaca aagaaaacga aaaaatcaag ttcactcttg gtgggtatac cagctttata 540
cgaaacaaca caaaaaatat tgtttatcca tttgaccaat atatcgccca ttggataatc 600
ggatatgtat atacaagagt tgctacaaga aaatcatctt taaaaacata taatataaat 660
gaactcaatg aaatccctaa accatacaaa ggcgtaaagg ttttcttaca agataaatgg 720
gttattgctg gagatttggc aggatctgga aacacaacaa atataggtag cattcatgcc 780
cactataaag actttgtaga aggaaaagga atatttgact cagaggatga gtttttagac 840
tattggagaa attatgaaag aaccagtcaa ttaagaaatg acaagtataa taatataagc 900
gaatacagaa actggatata ccgaggaaga aaataactag cataacccct ctctaaacgg 960
aggggttt 968

<210> SEQ ID NO 17
<211> LENGTH: 983
<212> TYPE: DNA
<213> ORGANISM: Haemophilus haemolyticus

<400> SEQUENCE: 17
gcgaattaat acgactcact ataggggaat tgtgagcgga taacaattcc cctctagaaa 60
taattttgtt taactttaag aaggagatat acgatgggca gcagccatca tcatcatcat 120
cacagcagcg gcatcgaagg tcgcagtggg ggcggagggt ccatgaactg gaaagaattc 180
gaagttttct gcgttaccta tttaaacaag acttatggca acaagtttgc gaagaagggg 240
gagagcgaca gcactacttc agacattttg ttcaccggaa ataatccctt ctacattgag 300
gcaaagatgc cgcactcgca atgcggccag tttgtattaa tccccaaccg tgctaaatac 360
aagtttgatt acagcccaaa gaacaaaagc gagattaatc catatacaca gaagattatg 420
caatttatgt ccgagaattt cagcgaatac gccaacttaa gcaccaaagg aaagattatt 480

```
ccattgcccg aatctgtctt tgtaaactgg atcaaggaat attataagtc gaaatcggtt    540

aagttcttta tcacttcgaa cggtgatttc attatcttcc ctatcgaaca tttcgaacac    600

tatttcaatg ttagctgtac ctatcgtatc aaaaaaagtg ggcctcgcca tctgaatagt    660

aaaagcttac ccgattttaa acaagcgtta gataagaaag gtatctccta cacaatgcga    720

ggccttgaac ttcattccga cgagaatatc cacgataagc gtatctcggg agacgacaag    780

gattttctga ttaaagagaa caacggggcc tatcacgtta agatcttgag taacacgttc    840

aacgccaatg tcattatctt caatatcatc aaaaagagtg gaggaggagg cagtgaaaac    900

ttatacttcc agagcagcag cggcgactac aaagatgatg atgataaata actagcataa    960

cccctctcta aacggagggg ttt                                            983
```

<210> SEQ ID NO 18
<211> LENGTH: 1043
<212> TYPE: DNA
<213> ORGANISM: Haemophilus influenzae

<400> SEQUENCE: 18

```
gcgaattaat acgactcact ataggggaat tgtgagccga taacaattcc cctctagaaa     60

taattttgtt taactttaag aaggagatat acgatgggca gcagccatca tcatcatcat    120

cacagctctg gcatcgaagg gcgcagtggg ggaggagggt ccatgagttt cataaaacct    180

atttatcagg atattaattc aatattaatc gggcaaaaag tgaaacgtcc taaatcaggt    240

actctgtcag gtcatgctgc aggggaacca tttgaaaaat tagtatataa gtttttgaaa    300

gaaaacctgt cagatttaac atttaagcaa tatgaatatc ttaatgattt atttatgaag    360

aaccctgcga taattggaca tgaagctaga tataaattat ttaattctcc aacattgctt    420

tttttgttaa gtagaggtaa agctgcaact gaaaattgga gcatagaaaa tttatttgag    480

gagaaacaaa atgatactgc agatatttta ttagtaaagg atcagttcta tgaattgtta    540

gatgtcaaaa caagaaatat tagtaaatca gctcaagcac ccaatattat ttcagcatat    600

aaattagctc agacgtgtgc aaaaaatgatt gataataaag aatttgattt atttgatatt    660

aattatttag aagtagactg ggaacttaat ggtgaagatc tagtttgtgt atctacttct    720

tttgctgaac tatttaaatc tgaacctagt gaactatata ttaactgggc tgcagctatg    780

caaattcagt ttcatgtaag agatttagat caggggttta atggaactag agaagaatgg    840

gcaaaatctt atctaaaaca ttttgttact caagcagagc aaagagccat atctatgata    900

gataagtttg ttaagccatt taagaaatat atacttagtg gaggaggagg cagtgaaaac    960

ttatacttcc agagcagctc tggcgactac aaagatgatg atgataaata actagcataa   1020

cccctctcta aacggagggg ttt                                           1043
```

<210> SEQ ID NO 19
<211> LENGTH: 1055
<212> TYPE: DNA
<213> ORGANISM: Haemophilus influenzae

<400> SEQUENCE: 19

```
gcgaattaat acgactcact ataggggaat tgtgagccga taacaattcc cctctagaaa     60

taattttgtt taactttaag aaggagatat acgatgggca gcagccatca tcatcatcat    120

cacagctctg gcatcgaagg gcgcagtggg ggaggagggt ccatgaatga tgaaatttcc    180

gacctaataa accaagccgt ttctaatatt ttaatcaata gtagtagtga aaacaaacta    240
```

```
aaaaaattga ttaaaacgca tgatgtaaaa attcattttg taccgagaaa ttaccgtatt    300

tttggtggaa ttttgcaaag tatgaacatt caatttggta attttttaga agaatttatg    360

acccttctaa taaaatctga tggcgttat gatattttgg aagaatacag tggtaaaaaa     420

agtaataaat ttcaattgtc tacaagtaat gacaatcgaa ttgaccaatt cataagtttt    480

tgtcagcgta gtgatagcat taatctcgat gaagaatttc caaaacttct aaatgaagta    540

aaaaatgata atgatacaaa tctttcttca attagccacg atattgacat tttatttaga    600

aataaagaaa ctggcgttat ttattattta gaagtgaaat acaatgacga ccacgacaca    660

ggaaaatttg ttgatataaa cagaaaattt attaaaacat acgcttattt ggtgcgtgaa    720

tttccaaaca cagaaattaa accaatactt ttctttttca ataacaagaa aatgaaaggg    780

aatatttatg ttccagaaaa tactaatatt aggcgtggta aatcgttttt tgatgaattt    840

ttaaaaatca aatatgaaga tgttgatagc tatatacgaa acctttcaga aagtcccgat    900

aatattaaag cctttgatga tttatacaga aaaataatgg ctatgaaaag tggaggagga    960

ggcagtgaaa acttatactt ccagagcagc tctggcgact acaaagatga tgatgataaa   1020

taactagcat aacccctctc taaacggagg ggttt                              1055
```

<210> SEQ ID NO 20
<211> LENGTH: 1052
<212> TYPE: DNA
<213> ORGANISM: Micrococcus sp.

<400> SEQUENCE: 20

```
gcgaattaat acgactcact ataggggaat tgtgagcgga taacaattcc cctctagaaa     60

taattttgtt taactttaag aaggagatat acgatgggca gcagccatca tcatcatcat    120

cacagcagcg gcatcgaagg gcgcagtggg ggcggagggt ccatgggtga catggcctac    180

cgtgatcgcc cgttaaacgc tgaagagatg gaagcattgc gtttggtgtt gtcaacgtat    240

cgcgattctt caggacaaaa ccaaacgaaa tacgggtcga tgccaggatt tcgtgatttc    300

gaacgcggct tggcttccgt actgggaggt actgcggctg aaaacaaagg agtcttcgac    360

attattgtaa ccccatcaga tgggagcacc gctttcggca tctcctgcaa aatggcacgt    420

ttcgcgccta aggcacaaaa cgcggccttt gtggagctgt caaatgccgc ggctaagttt    480

cgtgctcatt tgttagagcg ccagattaac tgggccacag acccgatgct tgctggtccc    540

gccattattg aactggttac aaagtggcac accgatgatg ccaatgagca tggattggac    600

ttggacaagt cagcgtacgc agtgttatct cgtagctcag actggagtac ttatcaactt    660

tccacttttc cactggacct ttacgggttt aatccgattg gagatattgc gtggacagcc    720

acaactaaac gcattgacgg gcatgttgaa attaacggcc aaccgcactt gttatggcag    780

tggtacccta cctccggtgg gcaattaaag tggtggccgc cgctgtcgtg ggctacgtgg    840

agtactgaac cttttactct tgaggaacca ccccttgtcc gtccagtaga acgcgccgag    900

gaatatttcc ccgatttgtg gccccacggg ttcactccca gcgcaagtgg aggaggaggc    960

agtgaaaact tatacttcca gagcagcagc ggcgactaca aagatgatga tgataaataa   1020

ctagcataac ccctctctaa acggaggggt tt                                 1052
```

<210> SEQ ID NO 21
<211> LENGTH: 1133
<212> TYPE: DNA
<213> ORGANISM: Nocardia corallina

<400> SEQUENCE: 21

```
gcgaattaat acgactcact ataggggaat tgtgagcgga taacaattcc cctctagaaa     60
taattttgtt taactttaag aaggagatat acgatgggca gcagccatca tcatcatcat    120
cacagcagcg gcatcgaagg gcgcagtggg ggcggagggt ccgtggcaac cgctccaggg    180
caccttttgg gacagattat tgggaatgtt atggaagaag ctcttaaacc tgtattgcag    240
gagatggctg atcgtcacga tctgtacctg gattccaaag gattacgtcc aggtgtacgt    300
tcgggcgctc ttgtcacctg gacagacgac ctgggtaaca accatgatct ggatttcgtc    360
cttgaacgcg gagggtctgc gacgaaagct gggaaccccg cggctttcat tgaggcagca    420
tggcgccgct atacaaaaca ctccaaagcg aaggcccaag aaatccaagg cgcggtgctt    480
ccggtgttag ctgcttggaa caacgtcaag cccaccccag ccgcggtcgt ggctggacaa    540
tggaccgctc ctagcttgca acaaatgcgt agtaacgggt tcgttgttct tcatctgcat    600
ttcccaacga cagcgcaagt ctttggcggg aatggcatta acatcgaagg caccggggaa    660
ggtactcctg acgcgttctg gcaacaacaa tgtgacgctt acacatcaaa gagcgaagcg    720
gacaaagatt ctctggcaac tgcccttcgc accgcacacg ctcaagaatt tcgtacattt    780
gttgcagaat tagagcgccg cgtagttcgc gccattgatt acgttgtagt gactccattg    840
catgggcatg gaagtcagta cacatccatc gaaaatgcca tcgaggccgt gcgcacatac    900
tcgtgtggcg aggagagcgc acccttcctt cgttttgaaa ttcgcatcag ttacacaaac    960
ggtgatgtaa tccaagccac atttgggtcc tcctcggacg ctattgaatt tttagacacg   1020
ttcaacagtg gaggaggagg cagtgaaaac ttatacttcc agagcagcag cggcgactac   1080
aaagatgatg atgataaata actagcataa cccctctcta aacggagggg ttt          1133
```

<210> SEQ ID NO 22
<211> LENGTH: 1253
<212> TYPE: DNA
<213> ORGANISM: Neisseria mucosa

<400> SEQUENCE: 22

```
gcgaattaat acgactcact ataggggaat tgtgagcgga taacaattcc cctctagaaa     60
taattttgtt taactttaag aaggagatat acgatgggca gcagccatca tcatcatcat    120
cacagcagcg gcatcgaagg gcgcagtggg ggcggagggt ccatgagctc ctaccatgat    180
gatcttaaca ttctgaacgt agacttcaac cacttacgcc tgaccgagct tatcaaattg    240
gctgatcaag cggaaccatt ttatctgtgg gtagaaaaga tattccgtca ggtaagtggt    300
cgcgcagact ccttggaaac catcatcgaa gttgaagaac gtgttgtcct taaaatggca    360
atcttaactt gttttacttc agatgaaaaa gagcttccga agttatttaa tggggtcgga    420
gtcccgtacc cccacattaa ggcgtgctat ttctttttcg cttggttggt gcgtgacgcg    480
gcgactcagc gtctcgatcc tttaattcgc gaggcgttca cgcaattgaa gtctattcat    540
ccacagatga aaaaaactga actggaatct gaaattttta gtcaacttct tgtgaactat    600
cgcaatgagt taattcactt ttcgtggcca gtcattcgtg aagttcttat ctcccgcctg    660
gaaggttccc gtcgtgcagc acgcgggtcc taccttgagc tttttgtgcg tacggctttg    720
gcgcaatcca tcacctactt ttacaaaatc tatggcaatt atgggaagtt cctggacgta    780
aaaattcacg ataagccctt gaaggttaaa aaccgcacat atgacgtcgt tgcggagctt    840
attgggaata atcacaatac acaatatctg attttgcccg tgaagacccg cgagacacag    900
ggtggtggtc atgcacacct gttcacccgc gatatagaac aaagtaacaa cgacatccgc    960
```

```
gaactttacc cgaatgcagt tatcgcaccc gttatcattg ccgaaaattg gtccgataca   1020

gagaaggatc ttgagaatgt gggttacaac gacatctttc acttttcagt caaccctaac   1080

cgctttgcgg gtttctctga tgtggaacaa atccgcttaa atcgtcttgt cgagcgcatc   1140

ttgctgagtg gaggaggagg cagtgaaaac ttatacttcc agagcagcag cggcgactac   1200

aaagatgatg atgataaata actagcataa cccctctcta aacggagggg ttt          1253
```

<210> SEQ ID NO 23
<211> LENGTH: 1418
<212> TYPE: DNA
<213> ORGANISM: Nocardia otitidiscaviarum

<400> SEQUENCE: 23

```
gcgaattaat acgactcact ataggggaat tgtgagcgga taacaattcc cctctagaaa     60

taattttgtt taactttaag aaggagatat acgatgggca gcagccatca tcatcatcat    120

cacagcagcg gcatcgaagg gcgcagtggg ggcggagggt ccatgcgtag tgatacatca    180

gttgagccgg agggggctaa ttttatcgca gagttcttcg gacaccgtgt ttacccggag    240

gtcgtgtcta cagaagctgc ccgcaatgac caggcgacag gtacttgtcc gttcttgaca    300

gctgccaaat tagtggagac atcttgcgtc aaagctgaaa cctcccgcgg cgtttgcgta    360

gttaacacgg ctgttgataa tgaacgttac gactggcttg tgtgcccgaa ccgcgcattg    420

gacccgcttt ttatgtcggc tgcttcacgt aaactttttg ggtacggtcc cacggagccg    480

cttcagttca ttgctgcacc cacccttgca gaccaagcag tacgtgacgg tattcgcgaa    540

tggcttgacc gcggagtaca tgtggtcgca tatttccagg aaaagttggg gggtgagttg    600

tcaatctcta agactgactc gtcacccgag ttctccttcg actggacatt ggcagaggta    660

gaaagtatct atcctgtgcc taaaattaaa cgttatggtg tcttggaaat tcagactatg    720

gacttccacg ggtcttataa acacgccgtc ggcgccatcg acattgctct ggttgaagga    780

attgactttc acgggtggtt gccgacccca gctggtcgtg ctgcgttgtc gaagaagatg    840

gaaggaccca atctgagtaa cgtctttaag cgcacattct atcaaatggc ttacaagttc    900

gctctttctg gacaccaacg ttgtgcaggg actggtttcg ccattccaca gagtgtttgg    960

aaatcctggt tacgccatct tgcaaaccct acattgatcg acaacggcga cggcactttc   1020

tccttggggg acacccgtaa tgattctgaa aatgcgtgga tttttgtatt tgaattagac   1080

ccagacactg atgcttcgcc tcgtccgctg gctccccacc ttgaaatccg tgtgaacgtc   1140

gatacactta ttgacttggc cttgcgtgaa agccctcgtg cagctctagg cccatctggc   1200

cctgtggcta cttttacaga taaagtagag gctcgcatgt tgcgtttctg gcctaagacg   1260

cgtcgtcgcc gttcgacgac accgggcggt caacgcggtc tttttgacgc tagtggagga   1320

ggaggcagtg aaaacttata cttccagagc agcagcggcg actacaaaga tgatgatgat   1380

aaataactag cataacccct ctctaaacgg aggggttt                          1418
```

<210> SEQ ID NO 24
<211> LENGTH: 1247
<212> TYPE: DNA
<213> ORGANISM: Providencia stuartii

<400> SEQUENCE: 24

```
gcgaattaat acgactcact ataggggaat tgtgagcgga taacaattcc cctctagaaa     60

taattttgtt taactttaag aaggagatat acgatgggca gcagccatca tcatcatcat    120

cacagcagcg gcatcgaagg gcgcagtggg ggcggagggt ccatgaaaga actgaaactg    180
```

```
aaagaagcga aagaaattct gaaagcactg ggcctgccgc cgcagcagta taacgatcgc    240
agcggctggg tgctgctggc gctggcgaac attaaaccgg aagatagctg gaaagaagcg    300
aaagcgccgc tgctgccgac cgtgagcatt atggaattta tacgaaccga atatggcaaa    360
gattataaac cgaacagccg cgaaaccatt aggcgccaga ccctgcatca gtttgaacag    420
gcgcgcattg tggatcgcaa ccgcgatctg ccgagccgcg cgaccaacag caaagataac    480
aactatagcc tgaaccaggt gattattgat attctgcata actatccgaa cggcaactgg    540
aaagaactca tccagcagtt tctgacccat gtgccgagcc tgcaagaact gtatgaacgc    600
gcgctggcgc gcgatcgcat tccgattaaa ctgctggatg gcacccagat tagcctgagc    660
ccgggcgaac ataaccagct gcatgcggat attgtgcatg aattttgccc gcgctttgtg    720
ggcgatatgg gcaaaattct gtatattggc gataccgcga gcagccgcaa cgaaggcggc    780
aaactgatgg tgctggatag cgaatatctg aaaaaactgg gcgtgccgcc gatgagccat    840
gataaactgc cggatgtggt ggtgtatgat gaaaaacgca aatggctgtt tctgattgaa    900
gcggtgacga gccacggccc gattagcccg aaacgctggc tggaactgga agcggcgctg    960
agcagctgca ccgtgggcaa agtgtatgtg accgcgtttc cgacccgcac cgaatttcgc   1020
aaaaacgcgg cgaacattgc gtgggaaacc gaagtgtgga ttgcggataa cccggatcat   1080
atggtgcatt ttaacggcga tcgctttctc ggcccgcatg ataaaaaacc ggaactgagc   1140
agtggaggag gaggcagtga aaacttatac ttccagagca gcagcggcga ctacaaagat   1200
gatgatgata aataactagc ataacccctc tctaaacgga ggggttt                 1247
```

<210> SEQ ID NO 25
<211> LENGTH: 1218
<212> TYPE: DNA
<213> ORGANISM: Streptomyces albus G

<400> SEQUENCE: 25

```
cgaaattaat acgactcact ataggggaat tgtgagcgga taacaattcc cctctagaaa     60
taattttgtt taactttaag aaggagatat accatgggca gcagccatca tcatcatcat    120
cacagcagcg gcatcgaagg gcgcagtggg ggcggagggt ccatgataaa cgccgataaa    180
ccacacagat ggaacgacga tgtacaggcg agcgtccgtc tttataacca atggttctta    240
gatgcagcgc caaaagcgta cagagacacg agacagctta ccatagacga ggttgaacag    300
gccttccagc gtacggctaa tatgacttct ataacgccag aggtacttaa agcacacccg    360
aagacattgg ccacgcttcg tatgtccaca gcgccaccca tcgcacggga ccggttggtg    420
ggactgtcac acgggagcaa gtccctgtta gacacgatgg aaaaggggaa gctgccgccg    480
agaatgaaag gtgacgtttt ggatactcat ttggcgaaaa tgtgcgcggt actgacagac    540
ctgttagacc ttgacttgtt tcactggtat ccaactggag agccagccga gccgcgtcaa    600
cgtgaactgg ctgccaccgt ggtagcggat cgtttgtgcg gcgcaatagc cgaccctatc    660
gtacgcaacg cccaagaaag acggcaactg gcgttgatag aggagtggct gcttgcaaga    720
ggatatacga agaaaactca ctctgcttcc ttgcctttga acaccatgca accaggcaca    780
ttttcgtttc gccagaatgt tgttgtcggc agtgacttac ctgttaatat ccccgtggac    840
gcagtaatac agccgcatac gcctcactct cacaagttac ccatacttat cgaagccaag    900
agtgctggag attttacaaa cacaaataag cgtcgtaaag aagaagcaac caagattcat    960
cagttgcaat taaagtatgg taacgagatc tcgctgacat tatttttatg tggctacttc   1020
```

aatacagggt acctgggcta ttctgcggcg gaaggcttag attgggtatg ggaacatcgc 1080
attgatgact tggaggctgc gggggcgagt ggaggaggag gcagtgaaaa cttatacttc 1140
cagagcagca gcggcgacta caaagatgat gatgataaat aactagcata acccctctct 1200
aaacggaggg gtttctga 1218

<210> SEQ ID NO 26
<211> LENGTH: 830
<212> TYPE: DNA
<213> ORGANISM: Serratia fonticola

<400> SEQUENCE: 26
gcgaattaat acgactcact ataggggaat tgtgagcgga taacaattcc cctctagaaa 60
taattttgtt taactttaag aaggagatat acgatgggca gcagccatca tcatcatcat 120
cacagcagcg gcatcgaagg gcgcagtggg ggcggagggt ccatgaataa cacccttgat 180
gaggcttttg ctttctacgc ttcgcacatc tacgacgaag agaagatcaa tcttttacgc 240
agccataatt taaaagtagc gggccacgtt ccttcggtct tgtgggaatt gttcgggtca 300
attttgaccg gccgtcgcgg taatgggatt acaggagcag acttacaagg ctgggaggtg 360
aagtcttcga ccctgcgtag ctcatttgaa tatcaatacc acttgaacac cggagaggct 420
aaactgttag aggactgtga ggtaaaccac ctgttctgct cttactctac ggactaccgt 480
gatcttatcg ttaaagcgat cccaggcgag gagttgaaag agacattctt tgaggcatgg 540
ctgcctgaat atcgcgcaaa ttatgatcgt accgtgggaa gcacaagtcg ccgtcagcgc 600
ttccgtaagg caattcctta tggcttcgtg caggtccatg gacgtacaat cttggaagtc 660
aaagcaggtg aaatgtatag ccgcaacgat agcttgttag aagagtttaa tcgccttgta 720
ggcagtggag gaggaggcag tgaaaactta tacttccaga gcagcagcgg cgactacaaa 780
gatgatgatg ataaataact agcataaccc ctctctaaac ggaggggttt 830

<210> SEQ ID NO 27
<211> LENGTH: 1226
<212> TYPE: DNA
<213> ORGANISM: Xanthomonas campestris

<400> SEQUENCE: 27
gcgaattaat acgactcact ataggggaat tgtgagcgga taacaattcc cctctagaaa 60
taattttgtt taactttaag aaggagatat acgatgggca gcagccatca tcatcatcat 120
cacagcagcg gcatcgaagg gcgcagtggg ggcggagggt ccatgaccat tccgaccctg 180
ggcagcctgg aaagcagcga agaactgatt aaggatctat atgtggatct gcgcaaacgc 240
attagcgtgt gggcggcggt gactaaacag accgcgcagg cgcgcatggg ctatattggc 300
cagcatctgg tgagcgtggt gacaggctat ccgggaggcc gcagcggcgc gcgcggcaaa 360
gacctggtgc tgccgaacga tgaatttgcg gaaattaaaa cgtgctatcg cgtggatcag 420
ctgggcaaat gcaacgattg cggcagcggc gtgagcgcgc tggaactgga atgcccgagc 480
tgcgcgagcg cgaacattaa acgcaacgat gatagcaaat ggctgattgg cattcagcat 540
gatgcggaat ttgcggaagt gctgaaaccg aaacattatt atctggtgct gtttgatttt 600
accgatctgc gccgcccgga taccattcgc gcgagcattt ggcgcgtgga tagcctgagc 660
ccgggctttg cgtattgcct gattgattat tataaaaaca ttaaaagcgc gagcaaaagc 720
ggcgcgccgt ttaacctgtg gccgtttcag ctgaaatttg aactgatgcg cccgctgctg 780
atttatcaga gctttattct gccggataac accattcaga cccgcgtgtt tccgggccat 840
cagccggcgg aacattatcc gctgagcccg ctgaccacct ttagccgcag ccagaacctg 900
accgcgggca aagtgcgcga atttgcggcg cgcctggaag tggaactgcc gattaacgcg 960
agcaaagcgg tgctgctgaa aaccgcgcag gatgcgatta ccgcgcgcaa actggatagc 1020
gatgtggtgg tggatgcgct ggcgcatccg ctgtgcgatg gcgattgcgc ggcgtttagc 1080
tggaccgcga gctttgatgc gccggcggat ggcggcagca gtggaggagg aggcagtgaa 1140
aacttatact tccagagcag cagcggcgac tacaaagatg atgatgataa ataactagca 1200
taacccctct ctaaacggag gggttt 1226

<210> SEQ ID NO 28
<211> LENGTH: 232
<212> TYPE: DNA
<213> ORGANISM: Artificial Sequence
<220> FEATURE:
<223> OTHER INFORMATION: AciI Toehold Swtich

<400> SEQUENCE: 28
aattgactct cttccgggcg ctatcatgcc ataccgcgaa aggttttgcg ccattcgatg 60
gtgtccggga tctcgacgct ctcccttatg aagtctaacg ctgctctggg ctaactgtcg 120
cgctaatacg actcactata gggtataagt aaatcgcttg ctgtatgtcg ttaaacagag 180
gagataacga atgacagcaa gcaacctggc ggcagcgcaa aagatgcgta aa 232

<210> SEQ ID NO 29
<211> LENGTH: 65
<212> TYPE: RNA
<213> ORGANISM: Artificial Sequence
<220> FEATURE:
<223> OTHER INFORMATION: AciI Trigger RNA

<400> SEQUENCE: 29
gggaugcccg uaguucauuc uacgggcaug aauaacgaca uacagcaagc gauuuacuua 60
uacua 65

<210> SEQ ID NO 30
<211> LENGTH: 239
<212> TYPE: DNA
<213> ORGANISM: Artificial Sequence
<220> FEATURE:
<223> OTHER INFORMATION: BanII Tohoeld Switch

<400> SEQUENCE: 30
aattgactct cttccgggcg ctatcatgcc ataccgcgaa aggttttgcg ccattcgatg 60
gtgtccggga tctcgacgct ctcccttatg aagtctaacg ctgctctggg ctaactgtcg 120
cgctaatacg actcactata gggcttacta ctttgacacc tgattctgac acgataacag 180
aacagaggag atatcgtatg agaatcagga acctggcggc agcgcaaaag atgcgtaaa 239

<210> SEQ ID NO 31
<211> LENGTH: 65
<212> TYPE: RNA
<213> ORGANISM: Artificial Sequence
<220> FEATURE:
<223> OTHER INFORMATION: BanII Trigger RNA

<400> SEQUENCE: 31
gggucaauua cccgugguag gguaauugaa agcgugucag aaucaggugu caaaguagua 60
aguag 65

<210> SEQ ID NO 32
<211> LENGTH: 232
<212> TYPE: DNA
<213> ORGANISM: Artificial Sequence
<220> FEATURE:
<223> OTHER INFORMATION: BstEII Toehold Switch

<400> SEQUENCE: 32
aattgactct cttccgggcg ctatcatgcc ataccgcgaa aggttttgcg ccattcgatg 60
gtgtccggga tctcgacgct ctcccttatg aagtctaacg ctgctctggg ctaactgtcg 120
cgctaatacg actcactata gggtgatgga ataaggctgt gtatatgatg ttagacagag 180
gagataacat atgatacaca gcaacctggc ggcagcgcaa aagatgcgta aa 232

<210> SEQ ID NO 33
<211> LENGTH: 65
<212> TYPE: RNA
<213> ORGANISM: Artificial Sequence
<220> FEATURE:
<223> OTHER INFORMATION: BstEII Trigger RNA

<400> SEQUENCE: 33
gggucaguuc cugagguacc aggaacugaa acuaacauca uauacacagc cuuauuccau 60
cacac 65

<210> SEQ ID NO 34
<211> LENGTH: 239
<212> TYPE: DNA
<213> ORGANISM: Artificial Sequence
<220> FEATURE:
<223> OTHER INFORMATION: ClaI/AciI Toehold Switch

<400> SEQUENCE: 34
aattgactct cttccgggcg ctatcatgcc ataccgcgaa aggttttgcg ccattcgatg 60
gtgtccggga tctcgacgct ctcccttatg aagtctaacg ctgctctggg ctaactgtcg 120
cgctaatacg actcactata gggagtttga ttacattgtc gtttagttta gtgatacata 180
aacagaggag atatcacatg actaaacgaa acctggcggc agcgcaaaag atgcgtaaa 239

<210> SEQ ID NO 35
<211> LENGTH: 65
<212> TYPE: RNA
<213> ORGANISM: Artificial Sequence
<220> FEATURE:
<223> OTHER INFORMATION: ClaI/AciI Trigger RNA

<400> SEQUENCE: 35
gggacagauc cacugaggcg uggaucugug aacacuaaac uaaacgacaa uguaaucaaa 60
cuaac 65

<210> SEQ ID NO 36
<211> LENGTH: 239
<212> TYPE: DNA
<213> ORGANISM: Artificial Sequence
<220> FEATURE:
<223> OTHER INFORMATION: EcoRV Toehold Switch

<400> SEQUENCE: 36
aattgactct cttccgggcg ctatcatgcc ataccgcgaa aggttttgcg ccattcgatg 60
gtgtccggga tctcgacgct ctcccttatg aagtctaacg ctgctctggg ctaactgtcg 120
cgctaatacg actcactata gggtatgtaa ttgatttggc ttctgttagt ttcatacaag 180
aacagaggag atatgaaatg aacagaagca acctggcggc agcgcaaaag atgcgtaaa 239

<210> SEQ ID NO 37
<211> LENGTH: 65
<212> TYPE: RNA
<213> ORGANISM: Artificial Sequence
<220> FEATURE:
<223> OTHER INFORMATION: EcoRV Trigger RNA

<400> SEQUENCE: 37
gggucCauuc uaggugauac uagaauggag cagaaacuaa cagaagccaa aucaauuaca 60
uacua 65

<210> SEQ ID NO 38
<211> LENGTH: 242
<212> TYPE: DNA
<213> ORGANISM: Artificial Sequence
<220> FEATURE:
<223> OTHER INFORMATION: HincII Toehold Switch

<400> SEQUENCE: 38
aattgactct cttccgggcg ctatcatgcc ataccgcgaa aggttttgcg ccattcgatg 60
gtgtccggga tctcgacgct ctcccttatg aagtctaacg ctgctctggg ctaactgtcg 120
cgctaatacg actcactata gggtgaattt gattgactag aatgatgata cgaacaagac 180
aagaacagag gagatcgtat atgcattcta gtaacctggc ggcagcgcaa aagatgcgta 240
aa 242

<210> SEQ ID NO 39
<211> LENGTH: 65
<212> TYPE: RNA
<213> ORGANISM: Artificial Sequence
<220> FEATURE:
<223> OTHER INFORMATION: HincII Trigger RNA

<400> SEQUENCE: 39
gggccacgcg uuguccuauc aacgcgugga aaucguauca ucauucuagu caaucaaauu 60
caaag 65

<210> SEQ ID NO 40
<211> LENGTH: 14
<212> TYPE: DNA
<213> ORGANISM: Artificial Sequence
<220> FEATURE:
<223> OTHER INFORMATION: AciI Capture

<400> SEQUENCE: 40
ctagcagtac accg 14

<210> SEQ ID NO 41
<211> LENGTH: 27
<212> TYPE: DNA
<213> ORGANISM: Artificial Sequence
<220> FEATURE:
<223> OTHER INFORMATION: AciI Inhibitor

<400> SEQUENCE: 41
ctagcagaac accgcggttc acgtccg 27

<210> SEQ ID NO 42
<211> LENGTH: 27
<212> TYPE: DNA

```
<213> ORGANISM: Artificial Sequence
<220> FEATURE:
<223> OTHER INFORMATION: AciI Reporter

<400> SEQUENCE: 42

cggacgtgaa ccgcggtgta ctgctag                                27


<210> SEQ ID NO 43
<211> LENGTH: 16
<212> TYPE: DNA
<213> ORGANISM: Artificial Sequence
<220> FEATURE:
<223> OTHER INFORMATION: BanII Capture

<400> SEQUENCE: 43

ggctcctcga gtatgc                                            16


<210> SEQ ID NO 44
<211> LENGTH: 29
<212> TYPE: DNA
<213> ORGANISM: Artificial Sequence
<220> FEATURE:
<223> OTHER INFORMATION: BanII Inhibitor

<400> SEQUENCE: 44

actgagaacg tggggctcct cgagtatgc                              29


<210> SEQ ID NO 45
<211> LENGTH: 29
<212> TYPE: DNA
<213> ORGANISM: Artificial Sequence
<220> FEATURE:
<223> OTHER INFORMATION: BanII Reporter

<400> SEQUENCE: 45

gcatactcga ggagccccac gttctcagt                              29


<210> SEQ ID NO 46
<211> LENGTH: 16
<212> TYPE: DNA
<213> ORGANISM: Artificial Sequence
<220> FEATURE:
<223> OTHER INFORMATION: BglII Capture

<400> SEQUENCE: 46

gcttgagaac tagatc                                            16


<210> SEQ ID NO 47
<211> LENGTH: 30
<212> TYPE: DNA
<213> ORGANISM: Artificial Sequence
<220> FEATURE:
<223> OTHER INFORMATION: BglII Inhibitor

<400> SEQUENCE: 47

gcttgagaac tagatctaag cacgtccagt                             30


<210> SEQ ID NO 48
<211> LENGTH: 30
<212> TYPE: DNA
<213> ORGANISM: Artificial Sequence
<220> FEATURE:
<223> OTHER INFORMATION: BglII Reporter

<400> SEQUENCE: 48

actggacgtg cttagatcta gttctcaagc                             30
```

<210> SEQ ID NO 49
<211> LENGTH: 14
<212> TYPE: DNA
<213> ORGANISM: Artificial Sequence
<220> FEATURE:
<223> OTHER INFORMATION: BsaAI Capture

<400> SEQUENCE: 49
cgtagggatc atac 14

<210> SEQ ID NO 50
<211> LENGTH: 29
<212> TYPE: DNA
<213> ORGANISM: Artificial Sequence
<220> FEATURE:
<223> OTHER INFORMATION: BsaAI Inhibitor

<400> SEQUENCE: 50
cgtagggata atacgtgagc tcacgtgca 29

<210> SEQ ID NO 51
<211> LENGTH: 29
<212> TYPE: DNA
<213> ORGANISM: Artificial Sequence
<220> FEATURE:
<223> OTHER INFORMATION: BsaAI Reporter

<400> SEQUENCE: 51
tgcacgtgag ctcacgtatg atccctacg 29

<210> SEQ ID NO 52
<211> LENGTH: 17
<212> TYPE: DNA
<213> ORGANISM: Artificial Sequence
<220> FEATURE:
<223> OTHER INFORMATION: BstEII Capture

<400> SEQUENCE: 52
cacatcgtca tggtgac 17

<210> SEQ ID NO 53
<211> LENGTH: 30
<212> TYPE: DNA
<213> ORGANISM: Artificial Sequence
<220> FEATURE:
<223> OTHER INFORMATION: BstEII Inhibitor

<400> SEQUENCE: 53
cacatcgaca tggtgacccg atgacctcgc 30

<210> SEQ ID NO 54
<211> LENGTH: 30
<212> TYPE: DNA
<213> ORGANISM: Artificial Sequence
<220> FEATURE:
<223> OTHER INFORMATION: BstEII Reporter

<400> SEQUENCE: 54
gcgaggtcat cgggtcacca tgacgatgtg 30

<210> SEQ ID NO 55
<211> LENGTH: 15
<212> TYPE: DNA
<213> ORGANISM: Artificial Sequence
<220> FEATURE:

<223> OTHER INFORMATION: ClaI Capture

<400> SEQUENCE: 55
gcaactgaac aatcg 15

<210> SEQ ID NO 56
<211> LENGTH: 29
<212> TYPE: DNA
<213> ORGANISM: Artificial Sequence
<220> FEATURE:
<223> OTHER INFORMATION: ClaI Inhibitor

<400> SEQUENCE: 56
gcaactgtac aatcgatgac tcagcaccg 29

<210> SEQ ID NO 57
<211> LENGTH: 29
<212> TYPE: DNA
<213> ORGANISM: Artificial Sequence
<220> FEATURE:
<223> OTHER INFORMATION: ClaI Reporter

<400> SEQUENCE: 57
cggtgctgag tcatcgattg ttcagttgc 29

<210> SEQ ID NO 58
<211> LENGTH: 14
<212> TYPE: DNA
<213> ORGANISM: Artificial Sequence
<220> FEATURE:
<223> OTHER INFORMATION: EcoRV Capture

<400> SEQUENCE: 58
tgcctggatt tgat 14

<210> SEQ ID NO 59
<211> LENGTH: 29
<212> TYPE: DNA
<213> ORGANISM: Artificial Sequence
<220> FEATURE:
<223> OTHER INFORMATION: EcoRV Inhibitor

<400> SEQUENCE: 59
tgcctggatt agatatccgt cgaggagac 29

<210> SEQ ID NO 60
<211> LENGTH: 29
<212> TYPE: DNA
<213> ORGANISM: Artificial Sequence
<220> FEATURE:
<223> OTHER INFORMATION: EcoRV Reporter

<400> SEQUENCE: 60
gtctcctcga cggatatcaa atccaggca 29

<210> SEQ ID NO 61
<211> LENGTH: 14
<212> TYPE: DNA
<213> ORGANISM: Artificial Sequence
<220> FEATURE:
<223> OTHER INFORMATION: HincII Capture

<400> SEQUENCE: 61
gtcgaggtac tgtt 14

<210> SEQ ID NO 62
<211> LENGTH: 29
<212> TYPE: DNA
<213> ORGANISM: Artificial Sequence
<220> FEATURE:
<223> OTHER INFORMATION: HincII Inhibitor

<400> SEQUENCE: 62
gtcgaggtaa tgttgacgat cctgagcga 29

<210> SEQ ID NO 63
<211> LENGTH: 29
<212> TYPE: DNA
<213> ORGANISM: Artificial Sequence
<220> FEATURE:
<223> OTHER INFORMATION: HincII Reporter

<400> SEQUENCE: 63
tcgctcagga tcgtcaacag tacctcgac 29

<210> SEQ ID NO 64
<211> LENGTH: 16
<212> TYPE: DNA
<213> ORGANISM: Artificial Sequence
<220> FEATURE:
<223> OTHER INFORMATION: NcoI Capture

<400> SEQUENCE: 64
cgaacacgtg accatg 16

<210> SEQ ID NO 65
<211> LENGTH: 29
<212> TYPE: DNA
<213> ORGANISM: Artificial Sequence
<220> FEATURE:
<223> OTHER INFORMATION: NcoI Inhibitor

<400> SEQUENCE: 65
cgaacacgtg accatggtgc agcatatgg 29

<210> SEQ ID NO 66
<211> LENGTH: 29
<212> TYPE: DNA
<213> ORGANISM: Artificial Sequence
<220> FEATURE:
<223> OTHER INFORMATION: NcoI Reporter

<400> SEQUENCE: 66
ccatatgctg caccatggtc acgtgttcg 29

<210> SEQ ID NO 67
<211> LENGTH: 16
<212> TYPE: DNA
<213> ORGANISM: Artificial Sequence
<220> FEATURE:
<223> OTHER INFORMATION: PstI Capture

<400> SEQUENCE: 67
aggcatgtca cctgca 16

<210> SEQ ID NO 68
<211> LENGTH: 29
<212> TYPE: DNA
<213> ORGANISM: Artificial Sequence
<220> FEATURE:
<223> OTHER INFORMATION: PstI Inhibitor

```
<400> SEQUENCE: 68

aggcatgtca cctgcaggag cttcagaac                                   29


<210> SEQ ID NO 69
<211> LENGTH: 29
<212> TYPE: DNA
<213> ORGANISM: Artificial Sequence
<220> FEATURE:
<223> OTHER INFORMATION: PstI Reporter

<400> SEQUENCE: 69

gttctgaagc tcctgcaggt gacatgcct                                   29
```